US009834610B2

(12) United States Patent
Tykocinski

(10) Patent No.: US 9,834,610 B2
(45) Date of Patent: Dec. 5, 2017

(54) FUSION PROTEINS FOR MODULATING REGULATORY AND EFFECTOR T CELLS

(71) Applicants: Thomas Jefferson University, Philadelphia, PA (US); The Trustees of the University of Pennsylvania, Philadelphia, PA (US)

(72) Inventor: Mark L. Tykocinski, Merion Station, PA (US)

(73) Assignees: Thomas Jefferson University, Philadelphia, PA (US); The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 14/764,024

(22) PCT Filed: Jan. 31, 2014

(86) PCT No.: PCT/US2014/014197
§ 371 (c)(1),
(2) Date: Jul. 28, 2015

(87) PCT Pub. No.: WO2015/116178
PCT Pub. Date: Aug. 6, 2015

(65) Prior Publication Data
US 2016/0347846 A1    Dec. 1, 2016

Related U.S. Application Data

(60) Provisional application No. 61/759,157, filed on Jan. 31, 2013.

(51) Int. Cl.
*C07K 16/46* (2006.01)
*C07K 16/28* (2006.01)
*C07K 14/705* (2006.01)
*C07K 14/525* (2006.01)
*A61K 39/395* (2006.01)
*A61K 38/19* (2006.01)
*C07K 14/52* (2006.01)

(52) U.S. Cl.
CPC .......... *C07K 16/2878* (2013.01); *C07K 14/52* (2013.01); *C07K 14/70575* (2013.01); *C07K 2317/75* (2013.01); *C07K 2319/00* (2013.01); *C07K 2319/22* (2013.01); *C07K 2319/31* (2013.01)

(58) Field of Classification Search
None
See application file for complete search history.

(56) References Cited

U.S. PATENT DOCUMENTS

| | | |
|---|---|---|
| 4,082,735 A | 4/1978 | Jones et al. |
| 4,082,736 A | 4/1978 | Jones et al. |
| 4,101,536 A | 7/1978 | Yamamura et al. |
| 4,185,089 A | 1/1980 | Derrien et al. |
| 4,235,771 A | 11/1980 | Adam |
| 4,406,890 A | 9/1983 | Tarcsay et al. |
| 4,444,887 A | 4/1984 | Hoffmann |
| 4,606,918 A | 8/1986 | Allison et al. |
| 4,716,111 A | 12/1987 | Osband et al. |
| 4,816,567 A | 3/1989 | Cabilly et al. |
| 4,962,091 A | 10/1990 | Eppstein et al. |
| 5,225,539 A | 7/1993 | Winter |
| 5,229,275 A | 7/1993 | Goroff |
| 5,350,674 A | 9/1994 | Boenisch et al. |
| 5,413,923 A | 5/1995 | Kucherlapati et al. |
| 5,457,035 A | 10/1995 | Baum et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,573,905 A | 11/1996 | Lerner et al. |
| 5,585,089 A | 12/1996 | Queen et al. |
| 5,585,362 A | 12/1996 | Wilson et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,766,886 A | 6/1998 | Studnicka et al. |
| 5,814,318 A | 9/1998 | Lonberg et al. |
| 5,939,598 A | 8/1999 | Kucherlapati et al. |
| 6,312,700 B1 | 11/2001 | Weinberg |
| 6,326,193 B1 | 12/2001 | Liu et al. |

(Continued)

FOREIGN PATENT DOCUMENTS

| | | |
|---|---|---|
| EP | 239400 | 9/1987 |
| EP | 592106 | 11/2004 |

(Continued)

OTHER PUBLICATIONS

Coe et al. Depletion of regulatory T cells by anti-GITR mAb as a novel mechanism for cancer immunotherapy. Cancer Immunol Immunother. Sep. 2010;59(9):1367-77. doi: 10.1007/s00262-010-0866-5.*
Kontermann RE. Dual targeting strategies with bispecific antibodies. MAbs. Mar.-Apr. 2012;4(2):182-97. doi: 10.4161/mabs.4.2. 19000. Epub Mar. 1, 2012.*
Michaelson et al. Anti-tumor activity of stability-engineered IgG-like bispecific antibodies targeting TRAIL-R2 and LTbetaR. MAbs. Mar.-Apr. 2009;1(2):128-41.*
Andre et al., "Measurement of cytotoxic activity in experimental cancer." 2004, J. Clin. Lab. Anal. 18:27-30.
Aslakson and Miller, "Selective Events in the Metastatic Process Defined by Analysis of the Sequential Dissemination of Subpopulations of a Mouse Mammary Tumor¹" 1992, Cancer Res. 52:1399-1405.

(Continued)

*Primary Examiner* — David Romeo
(74) *Attorney, Agent, or Firm* — Saul Ewing Arnstein & Lehr LLP; Kathryn Doyle

(57) ABSTRACT

The present invention provides fusion proteins that act on the glucocorticoid-induced TNFR family-related gene (GITR) and OX40 signaling pathway. In certain aspects, the proteins of the invention are useful in modulating both regulatory T (Treg) cells and effector T (Teff) cells.

6 Claims, 21 Drawing Sheets

(56) References Cited

U.S. PATENT DOCUMENTS

| | | | |
|---|---|---|---|
| 6,331,415 | B1 | 12/2001 | Cabilly et al. |
| 6,407,213 | B1 | 6/2002 | Carter et al. |
| 6,548,640 | B1 | 4/2003 | Winter |
| 7,241,444 | B2* | 7/2007 | Goetsch ............ A61K 47/48392 424/130.1 |
| 7,285,522 | B2 | 10/2007 | Van Buskirk |
| 2004/0038349 | A1* | 2/2004 | Hilbert ................. C07K 14/525 435/69.5 |
| 2005/0042664 | A1 | 2/2005 | Wu et al. |
| 2005/0048617 | A1 | 3/2005 | Wu et al. |
| 2009/0263348 | A1 | 10/2009 | Kornbluth |
| 2012/0189639 | A1 | 7/2012 | Schebye et al. |
| 2012/0237498 | A1* | 9/2012 | Ahrens ............ A61K 39/39558 424/130.1 |

FOREIGN PATENT DOCUMENTS

| | | |
|---|---|---|
| EP | 519596 | 2/2005 |
| WO | WO 91/09967 | 7/1991 |
| WO | WO 91/10741 | 7/1991 |
| WO | WO 93/17105 | 9/1993 |
| WO | WO 94/07529 | 4/1994 |
| WO | WO 95/21915 | 8/1995 |
| WO | WO 96/33735 | 10/1996 |
| WO | WO 96/34096 | 10/1996 |
| WO | WO 98/16654 | 4/1998 |
| WO | WO 98/24893 | 6/1998 |
| WO | WO 98/46645 | 10/1998 |
| WO | WO 98/50433 | 11/1998 |
| WO | WO 01/29058 | 4/2001 |
| WO | WO 01/96584 | 12/2001 |
| WO | 2006050172 A2 | 5/2006 |
| WO | WO 2006/121810 | 11/2006 |
| WO | WO 2011/109789 | 9/2011 |
| WO | 2012170072 A1 | 12/2012 |

OTHER PUBLICATIONS

Baca et al., "Antibody Humanization Using Monovalent Phage Display." J. Biol. Chem., 272(16):10678-84 (1997).
Bates et al., "Quantification of Regulatory T Cells Enables the Identification of High-Risk Breast Cancer Patients and Those at Risk of Late Relapse." 2006, J. Clin. Oncol. 24: 5373-5380.
Bird et al., "Single-chain Antigen-Binding Proteins." 1988, Science 242:423-426.
Bruggemann et al., "Designer Mice: The Production of Human Antibody Repertoires in Transgenic Animals." Year in Immunol., 7:33-40 (1993).
Burgess et al., "Detection and characterization of OX40 ligand expression in human airway smooth muscle cells: A possible role in asthma?" 2004, J. Allergy Clin. Immunol. 113:683-689.
Burocchi et al., "Intratumor OX40 stimulation inhibits IRF1 expression and IL-10 production by Treg cells while enhancing CD40L expression by effector memory T cells." 2011, Eur. J. Immunol. 41:3615-3626.
Caldas et al., "Design and synthesis of germline-based hemi-humanized single-chain Fv against the CD18 surface antigen." Protein Eng., 13(5):353-60 (2000).
Carter et al., "Humanization of an anti-p185$^{HER2}$ antibody for human cancer therapy." Proc. Natl. Acad. Sci. USA, 89:4285-4289 (1992).
Chothia et al., "Canonical Structures for the Hypervariable Regions of Immunoglobulins." J. Mol. Biol., 196:901-117 (1987).
Clackson et al., "Making antibody fragments using phage display libraries." Nature, 352:624-628 (1991).
Cohen et al., "Agonist Anti-GITR Monoclonal Antibody Induces Melanoma Tumor Immunity in Mice by Altering Regulatory T Cell Stability and Intra-Tumor Accumulation." 2010, PLoS One 5:e10436.
Compaan, D. et al., "The crystal structure of the Costimulatory OX40-OX40L complex", Structure 14: 1321-1330 (2006).

Couto et al., "Anti-BA46 Monoclonal Antibody Mc3: Humanization Using a Novel Positional Consensus and in Vivo and in Vitro Characterization." Cancer Res., 55(8):1717-22 (1995).
Couto et al., "Designing Human Consensus Antibodies with Minimal Positional Templates." Cancer Res., 55 (23 Supp):5973s-5977s (1995).
Creighton (1983) Proteins Structures and Molecular Principles, WH Freeman and Co, New York N.Y.
Daugherty et al., "Polymerase chain reaction facilitates the cloning, CDR-grafting, and rapid expression of a murine monoclonal antibody directed against the CD18 component of leukocyte integrins." Nucleic Acids Res. 19:2471-6 (1991).
Disis et al., "Use of tumour-responsive T cells as cancer treatment." 2009, Lancet 373: 673-683.
Duchosal et al., "Immunization of hu-PBL-SCID mice and the rescue of human monoclonal Fab fragments through combinatorial libraries." Nature, 355:258 (1992).
Fallarino and Gajewski, "Cutting Edge: Differentiation of Antitumor CTL In Vivo Requires Host Expression of Statl." 1999, J. Immunol. 163:4109-4113.
Gao et al., "Intratumoral Balance of Regulatory and Cytotoxic T Cells Is Associated With Prognosis of Hepatocellular Carcinoma After Resection." 2007, J. Clin. Oncol. 25:2586-2593.
GenBank Accession No. gi:23238190; published Sep. 20, 2002.
GenBank Accession No. gi:23238193; published Sep. 20, 2002.
GenBank Accession No. gi:23238196; published Sep. 20, 2002.
GenBank Accession No. gi:40354198; published Dec. 24, 2003.
Gillman et al., "Site-Specific Mutagenesis Using Synthetic Oligodeoxyribonucleotide Primers: I. Optimum Conditions and Minimum Oligodeoxyribonucleotide Length." Gene 8:81-97 (1979).
Griffiths et al., "Human anti-self antibodies with high specificity from phage display libraries." EMBO J., 12:725-734 (1993).
Hoogenboom et al., "By-passing immunization. Human antibodies from synthetic repertoires of germline VH gene segments rearranged in vitro." J. Mol. Biol., 227:381 (1991) (Absract).
Huston et al., "Protein engineering of antibody binding sites: Recovery of specific activity in an anti-digoxin single-chain Fv analogue produced in *Escherichia coli*." 1988, Proc. Natl. Acad. Sci. USA 85:5879-5883.
Ishii et al., "OX40-OX40 Ligand Interaction in T-Cell-Mediated Immunity and Immunopathology." 2010, Adv. Immunol. 105:63-98.
Jakobovits et al., "Analysis of homozygous mutant chimeric mice: Deletion of the immunoglobulin heavy-chain joining region blocks B-cell development and antibody production." Proc. Natl. Acad. Sci. USA, 90:2551-2555 (1993).
Jakobovits et al., "Germ-line transmission and expression of a human-derived yeast artificial chromosome." Nature, 362:255-258 (1993).
Ji et al., "Cutting Edge: The Natural Ligand for Glucocorticoid-Induced TNF Receptor-Related Protein Abrogates Regulatory T Cell Suppression." 2004, J. Immunol. 172:5823-5827.
Johnson, Kevin S, and Chiswell, David J., "Human antibody engineering." Current Opinion in Structural Biology 3:564-571 (1993).
Jones et al., "Replacing the complementarity-determining regions in a human antibody with those from a mouse." Nature, 321:522-525 (1986).
Kedar and Weiss, "The in vitro generation of effector lymphocytes and their employment in tumor immunotherapy." 1983, Adv. Cancer Res. 38:171-287.
Kitamura et al., "OX40 costimulation can abrogate Foxp3+ regulatory T cell-mediated suppression of antitumor immunity." 2009, Int. J. Cancer 125:630-638.
Ko et al., "Treatment of advanced tumors with agonistic anti-GITR mAb and its effects on tumor-infiltrating Foxp3+CD25+CD4+ regulatory T cells." 2005, J. Exp. Med. 202:885-891.
Konjevic et al., "Corrections to the original lactate dehydrogenase ( LDH) release assay for the evaluation of NK cell cytotoxicity." 1997, J. Immunol. Methods 200:199-201.
Lanzavecchia et al., "The use of hybrid hybridomas to target human cytotoxic T lymphocytes." Eur. J. Immunol. 17, 105-11 (1987) (Abstract).

(56) References Cited

OTHER PUBLICATIONS

Lonberg and Huszar, "Human Antibodies from Transgenic Mice." Int. Rev. Immunol., 13:65-93 (1995).
Malek and Castro, "Interleukin-2 Receptor Signaling: At the Interface between Tolerance and Immunity." 2010, Immunity 33:153-165.
Marks et al., "By-passing immunization. Human antibodies from V-gene libraries displayed on phage." J. Mol. Biol., 222:581-597 (1991) (Abstract).
McCafferty et al., "Phage antibodies: filamentous phage displaying antibody variable domains." Nature, 348:552-553 (1990).
Miller et al., "CD4+CD25$^{high}$ T Cells Are Enriched in the Tumor and Peripheral Blood of Prostate Cancer Patients." 2006, J. Immunol. 177:7398-7405.
Morea et al., "Antibody Modeling: Implications for Engineering and Design." Methods, 20(3):267-79 (2000).
Mumtaz et al., "Design of liposomes for circumventing the reticuloendothelial cells." 1991 Glycobiology 5: 505-10.
Ndhlovu et al., "Expanding role of T-cell costimulators in regulatory T-cell function: recent advances in accessory molecules expressed on both regulatory and nonregulatory T cells." 2004, Crit. Rev. Immunol. 24:251-266.
Nocentini and Riccardi, "GITR: A Modulator of Immune Response and Inflammation." 2009, Adv. Exp. Med. Biol. 647:156-173.
Nocentini et al., "GITR/GITRL: More than an effector T cell co-stimulatory system." 2007, Eur. J. Immunol. 37:1165-1169.
Nocentini et al., "Modulation of Acute and Chronic Inflammation of the Lung by GITR and its Ligand." 2007, Ann. N. Y. Acad. Sci. 1107:380-391.
Nocentini, G, et al., "A new member of the tumor necrosis factory nerve growth factor receptor family inhibits T cell receptor-induced apoptosis." 1997, Proc. Natl. Acad. Sci., USA 94:6216-6221.
Oble et al., "Focus on TILs: Prognostic significance of tumor infiltrating lymphocytes in human melanoma." 2009, Cancer. Immun. 9:3.
Padlan, "A possible procedure for reducing the immunogenicity of antibody variable domains while preserving their ligand-binding properties." 1991, Molecular Immunology, 28(4/5):489-498.
Pedersen et al., "Comparison of Surface Accessible Residues in Human and Murine Immunoglobulin Fv Domains: Implication for Humanization of Murine Antibodies." J. Mol. Biol., 235(3):959-73 (1994).
Piconese et al., "OX40 triggering blocks suppression by regulatory T cells and facilitates tumor rejection." 2008, J. Exp. Med. 205:825-839.
Ponte et al., "Enhancement of humoral and cellular immunity with an antiglucocorticoid-induced tumour necrosis factor receptor monoclonal antibody." 2010, Immunology 130:231-242.
Prell et al., "OX40-Mediated Memory T Cell Generation Is TNF Receptor-Associated Factor 2 Dependent." 2003, J. Immunol. 171:5997-6005.
Presta et al., "Humanization of an Antibody Directed Against IgE." J. Immunol., 151:2623-32 (1993).
Qin, "Dynamic Behavior and Function of Foxp3+ Regulatory T Cells in Tumor Bearing Host." 2009, Cell. Mol. Immunol. 6:3-13.
Ramirez-Montagut et al., "Glucocorticoid-Induced TNF Receptor Family Related Gene Activation Overcomes Tolerance/Ignorance to Melanoma Differentiation Antigens and Enhances Antitumor Immunity." 2006, J. Immunol. 176:6434-6442.
Riechmann et al., "Reshaping human antibodies for therapy." 1988, Nature, 332:323.
Roberts et al., "Generation of an antibody with enhanced affinity and specificity for its antigen by protein engineering." Nature 328:731-34 (1987).
Roder et al., "The EBV-Hybridoma Technique." Methods Enzymol., 121:140-167 (1986).
Roguska et al., "A comparison of two murine monoclonal antibodies humanized by CDR-grafting and variable domain resurfacing." Protein Eng., 9(10):895-904 (1996).
Roguska et al., "Humanization of murine monoclonal antibodies through variable domain resurfacing." 1994 PNAS, 91:969-973.
Sadun et al., "Fc-mOX40L Fusion Protein Produces Complete Remission and Enhanced Survival in 2 Murine Tumor Models." 2008, J. Immunother. 31:235-245.
Saiki et al., "Primer-Directed Enzymatic Amplification of DNA with a Thermostable DNA Polymerase." Science 239:487 (1988).
Sandhu J S, "A rapid procedure for the humanization of monoclonal antibodies." Gene, 150(2):409-10 (1994).
Shankaran et al., "IFNg and lymphocytes prevent primary tumour development and shape tumour immunogenicity." 2001, Nature 410:1107-1111.
Shevach, "Mechanisms of Foxp3+ T Regulatory Cell-Mediated Suppression." 2009, Immunity 30: 636-645.
Shimizu et al., "Stimulation of CD25+CD4+ regulatory T cells through GITR breaks immunological self-tolerance." 2002, Nat. Immunol. 3:135-142.
Sims et al., "A Humanized CD18 Antibody Can Block Function without Cell Destruction." J. Immunol., 151:2296 (1993).
Smyth et al., "NK cells and NKT cells collaborate in host protection from methylcholanthrene-induced fibrosarcoma." 2001, Int. Immunol. 13:459-463.
So et al., "Immune regulation and control of regulatory T cells by OX40 and 4-1BB." 2008, Cytokine Growth Factor Rev. 19:253-262.
Studnicka et al., "HJuman-engineered monoclonal antibodies retain full specific binding activity by preserving non-CDR complementary-modulating residues." 1994, Protein Engineering, 7(6):805-814.
Swiss Prot. Accession No. P15725; published Apr. 1, 1990.
Swiss Prot. Accession No. P43489; published Nov. 1, 1995.
Swiss Prot. Accession No. P47741; published Feb. 1, 1996.
Tan et al., "'Superhumanized' Antibodies: Reduction of Immunogenic Potential by Complementarity-Determining Region Grafting with Human Germline Sequences: Application to an Anti-CD28." J. Immunol., 169:1119-25 (2002).
Teicher, "Acute and chronic in vivo therapeutic resistance." 2009, Biochem. Pharmacol. 77:1665-1673.
Thompson et al. "CD28 activation pathway regulates the production of multiple Tcell-derived lymphokines/cytokines." Proc. Natl. Acad. Sci. USA. 86:1333 (1989).
Thornton et al., "Cutting Edge: IL-2 Is Critically Required for the In Vitro Activation of CD4☐CD25☐ T Cell Suppressor Function." 2004, J. Immunol. 172:6519-6523.
Tone et al., "Smad3 and NFAT cooperate to induce Foxp3 expression through its enhancer." 2008, Nat. Immunol. 9:194-202.
Ui-Tei et al., "Sensitive assay of RNA interference in *Drosophila* and Chinese hamster cultured cells using firefly luciferase gene as target." 2000, FEBS Letters 479: 79-82.
Valzasina et al., "Triggering of OX40 (CD134) on CD4(+)CD25+ T cells blocks their inhibitory activity: a novel regulatory role for OX40 and its comparison with GITR." 2005, Blood 105(7):2845-2851.
van Olffen et al., "GITR Triggering Induces Expansion of Both Effector and Regulatory CD4 T Cells In Vivo." 2009, J. Immunol. 182:7490-7500.
Vaughan et al., "Human antibodies with sub-nanomolar affinities isolated from a large non-immunized phage display library." Nature Biotech., 14:309 (1996) (Abstract).
Verhoeyen et al., "Reshaping Human Antibodies: Grafting an Antilysozyme Activity." Science, 239:1534-1536 (1988)).
Vu et al., "OX40 costimulation turns off Foxp3 Tregs." 2007, Blood 110:2501-2510.
Watts, "TNF/TNFR Family Members in Costimulation of T Cell Responses." 2005, Annu. Rev. Immunol. 23:23-68.
Whiteside, "Immune responses to malignancies." 2010, J. Allergy Clin. Immunol. 125:S272-83.
Winter and Milstein, "Man-made antibodies." Nature, 349, pp. 293-299 (1991).
Wu et al., "Humanization of a Murine Monoclonal Antibody by Simultaneous Optimization of Framework and CDR Residues." J. Mol. Biol., 294:151 (1999).

(56) References Cited

OTHER PUBLICATIONS

Yamaguchi and Sakaguchi, "Regulatory T cells in immune surveillance and treatment of cancer." 2006, Semin. Cancer Biol. 16:115-123.
Yu and Fu, "Tumor-infiltrating T lymphocytes: friends or foes?" 2006, Lab. Invest. 86:231-245.
Zhou et al., "Amplification of tumor-specific regulatory T cells following therapeutic cancer vaccines." 2006, Blood 107:628-636.
Zhou et al., "Pivotal Roles of CD4☐ Effector T cells in Mediating Agonistic Anti-GITR mAb-Induced-Immune Activation and Tumor Immunity in CT26 Tumors." 2007, J. Immunol. 179:7365-7375.
Zubairi et al., "Immunotherapy with OX40L-Fc or anti-CTLA-4 enhances local tissue responses and killing of *Leishmania donovani*." 2004, Eur. J. Immunol. 34:1433-1440.
International Search Report for PCT/US2014/014197 dated Apr. 25, 2014.
Frumento, et al., "Targeting tumor-related immunosuppression for cancer immunotherapy", Endocr Metab Immune Disord Drug Targets. 6(3), Sep. 2006, 233-237.
Hornig, et al., "Combination of a bispecific antibody and costimulatory antibody-ligand fusion proteins for targeted aancer immunotherapy", J Immunother. 35(5), Jun. 2012, 418-429.
Kanagavelu, et al., "Soluble multi-trimeric TNF superfamily ligand adjuvants enhance immune responses to a HIV-1 Gag DNA vaccine", Vaccine. 30(4), Jan. 2012, 691-702.
Yao, et al., "Advances in targeting cell surface signalling molecules for immune modulation", Nat Rev Drug Discov. 12 (2), Feb. 2013, 130-146.
Extended European Search Report issued for European Patent Application No. 14881154.0 issued Jun. 21, 2016.

\* cited by examiner

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: chemically synthesized

<400> SEQUENCE: 1
acaacacacg rgaccttagg ag                                                  22

<210> SEQ ID NO 2
<211> LENGTH: 21
<212> TYPE: DNA
<213> ORGANISM: Artificial Sequence
<220> FEATURE:
<223> OTHER INFORMATION: chemically synthesized

<400> SEQUENCE: 2
cactcattcc tgttgaagct c                                                   21

<210> SEQ ID NO 3
<211> LENGTH: 15
<212> TYPE: PRT
<213> ORGANISM: Homo sapiens
<220> FEATURE:
<221> NAME/KEY: misc_feature
<223> OTHER INFORMATION: hinge region of human IgG1

<400> SEQUENCE: 3

Glu Pro Lys Ser Cys Asp Lys Thr His Thr Cys Pro Pro Cys Pro
1               5                   10                  15

<210> SEQ ID NO 4
<211> LENGTH: 8
<212> TYPE: PRT
<213> ORGANISM: Homo sapiens
<220> FEATURE:
<221> NAME/KEY: misc_feature
<223> OTHER INFORMATION: strep-tag

<400> SEQUENCE: 4

Trp Ser His Pro Gln Phe Glu Lys
```

<210> SEQ ID NO 5
<211> LENGTH: 639
<212> TYPE: PRT
<213> ORGANISM: Mus musculus
<220> FEATURE:
<221> NAME/KEY: misc_feature
<223> OTHER INFORMATION: DTA-1 Heavy Chain-human IgG-mouse OX40L

<400> SEQUENCE: 5

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Ala Glu
            20                  25                  30

Pro Gly Arg Ser Leu Arg Leu Ala Cys Thr Ala Ser Gly Phe Thr Phe
        35                  40                  45

Gly Asn Tyr Ala Ile Thr Trp Phe Arg Gln Ala Pro Gly Lys Gly Leu
    50                  55                  60

Glu Trp Val Ala Phe Ile Arg Ser Lys Ile Tyr His Ala Ala Ser Asp
65                  70                  75                  80

His Ala Ala Ser Val Lys Gly Arg Phe Thr Ile Ser Arg Asp Asp Ser
                85                  90                  95

Asn Gly Val Ala Tyr Leu Gln Met Asn Ser Leu Gln Thr Glu Asp Thr
            100                 105                 110

Ala Val Tyr Tyr Cys Ser Arg Ala Ala Leu Tyr Asp Tyr Gly Asp Tyr
        115                 120                 125

Gly Asp Phe Asp Tyr Trp Gly His Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350
```

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
    450                 455                 460

Gln Lys Ser Leu Ser Leu Ser Pro Gly Lys Glu Pro Lys Ser Cys Asp
465                 470                 475                 480

Lys Thr His Thr Cys Pro Pro Cys Pro Gln Leu Ser Ser Ser Pro Ala
                485                 490                 495

Lys Asp Pro Pro Ile Gln Arg Leu Arg Gly Ala Val Thr Arg Cys Glu
            500                 505                 510

Asp Gly Gln Leu Phe Ile Ser Ser Tyr Lys Asn Glu Tyr Gln Thr Met
            515                 520                 525

Glu Val Gln Asn Asn Ser Val Val Ile Lys Cys Asp Gly Leu Tyr Ile
    530                 535                 540

Ile Tyr Leu Lys Gly Ser Phe Phe Gln Glu Val Lys Ile Asp Leu His
545                 550                 555                 560

Phe Arg Glu Asp His Asn Pro Ile Ser Ile Pro Met Leu Asn Asp Gly
                565                 570                 575

Arg Arg Ile Val Phe Thr Val Val Ala Ser Leu Ala Phe Lys Asp Lys
            580                 585                 590

Val Tyr Leu Thr Val Asn Ala Pro Asp Thr Leu Cys Glu His Leu Gln
            595                 600                 605

Ile Asn Asp Gly Glu Leu Ile Val Val Gln Leu Thr Pro Gly Tyr Cys
            610                 615                 620

Ala Pro Glu Gly Ser Tyr His Ser Thr Val Asn Gln Val Pro Leu
625                 630                 635

<210> SEQ ID NO 6
<211> LENGTH: 232
<212> TYPE: PRT
<213> ORGANISM: Homo sapiens
<220> FEATURE:
<221> NAME/KEY: misc_feature
<223> OTHER INFORMATION: DTA-1 Light Chain

<400> SEQUENCE: 6

Met Gly Leu Ser Trp Val Phe Leu Val Ala Leu Leu Lys Gly Ile Gln
1               5                   10                  15

Cys Glu Val Gln Leu Val Glu Thr Gly Gly Gly Leu Val Arg Pro Gly
            20                  25                  30

Ser Ser Leu Lys Leu Ser Cys Ala Thr Ser Gly Phe Thr Phe Ser Asn
            35                  40                  45

```
Thr Trp Met Asn Trp Val Arg Gln Ala Pro Gly Lys Gly Leu Glu Trp
 50                  55                  60

Val Ala Leu Ile Lys Glu Lys Tyr Thr Asn Tyr Glu Ala Lys Tyr Ala
 65                  70                  75                  80

Glu Ser Val Lys Gly Arg Phe Thr Ile Ser Arg Asp Asp Ser Lys Ser
                 85                  90                  95

Arg Val Tyr Leu Gln Met Asn Thr Leu Arg Asp Gln Asp Thr Ala Thr
            100                 105                 110

Tyr Tyr Cys Thr Val Gln Leu Gly Pro Phe Asp Tyr Trp Gly Gln Gly
        115                 120                 125

Val Thr Val Thr Val Ser Ser Ala Gln Thr Thr Ala Pro Ser Val Tyr
130                 135                 140

Pro Leu Ala Pro Gly Cys Gly Asp Thr Thr Ser Ser Thr Val Thr Leu
145                 150                 155                 160

Gly Cys Leu Val Lys Gly Tyr Phe Pro Glu Pro Val Thr Val Thr Trp
                165                 170                 175

Asn Ser Gly Ala Leu Ser Ser Asp Val His Thr Phe Pro Ala Val Leu
            180                 185                 190

Gln Ser Gly Leu Tyr Thr Leu Thr Ser Ser Val Thr Ser Ser Thr Trp
        195                 200                 205

Pro Ser Gln Thr Val Thr Cys Asn Val Ala His Pro Ala Ser Ser Thr
210                 215                 220

Lys Val Asp Lys Lys Val Gly Ser
225                 230
```

```
<210> SEQ ID NO 7
<211> LENGTH: 158
<212> TYPE: PRT
<213> ORGANISM: Mus musculus
<220> FEATURE:
<221> NAME/KEY: misc_feature
<223> OTHER INFORMATION: STREP-tag-mouse OX40L

<400> SEQUENCE: 7
```

```
Trp Ser His Pro Gln Phe Glu Lys Gln Leu Ser Ser Ser Pro Ala Lys
 1               5                  10                  15

Asp Pro Pro Ile Gln Arg Leu Arg Gly Ala Val Thr Arg Cys Glu Asp
                20                  25                  30

Gly Gln Leu Phe Ile Ser Ser Tyr Lys Asn Glu Tyr Gln Thr Met Glu
            35                  40                  45

Val Gln Asn Asn Ser Val Val Ile Lys Cys Asp Gly Leu Tyr Ile Ile
 50                  55                  60

Tyr Leu Lys Gly Ser Phe Phe Gln Glu Val Lys Ile Asp Leu His Phe
 65                  70                  75                  80

Arg Glu Asp His Asn Pro Ile Ser Ile Pro Met Leu Asn Asp Gly Arg
                 85                  90                  95

Arg Ile Val Phe Thr Val Val Ala Ser Leu Ala Phe Lys Asp Lys Val
            100                 105                 110

Tyr Leu Thr Val Asn Ala Pro Asp Thr Leu Cys Glu His Leu Gln Ile
        115                 120                 125

Asn Asp Gly Glu Leu Ile Val Val Gln Leu Thr Pro Gly Tyr Cys Ala
        130                 135                 140

Pro Glu Gly Ser Tyr His Ser Thr Val Asn Gln Val Pro Leu
145                 150                 155
```

FUSION PROTEINS FOR MODULATING REGULATORY AND EFFECTOR T CELLS

CROSS REFERENCE TO RELATED APPLICATIONS

This application is the U.S. national phase application filed under 35 U.S.C. §371 claiming priority to International Patent Application No. PCT/US2014/014197, filed Jan. 31, 2014, which claims priority under 35 U.S.C. §119(e) to U.S. Provisional Application No. 61/759,157, filed Jan. 31, 2013, all of which applications are hereby incorporated by reference in their entireties.

STATEMENT REGARDING FEDERALLY SPONSORED RESEARCH OR DEVELOPMENT

This invention was made with government support under grant numbers AI 031044 and CA 074958 awarded by the National Institutes of Health (NIH). The government has certain rights in the invention.

BACKGROUND OF THE INVENTION

Compelling evidence from model systems points to immune surveillance mechanisms that can recognize and eliminate tumor cells (Smyth et al., 2001, Int. Immunol. 13:459-463; Shankaran et al., 2001, Nature 410:1107-1111; Qin, 2009, Cell. Mol. Immunol. 6:3-13). Yet, established cancers commonly resist immune eradication, attributable in part to immunosuppressive elements within tumor microenvironments that limit the anti-tumor activity of infiltrating CD8$^+$ cytotoxic T lymphocytes (CTL) and other immune effectors. A variety of immunosuppressive mechanisms have been suggested to date, including tumor-intrinsic events (e.g., down-regulation of costimulators), soluble suppressive factors (e.g., transforming growth factor β), and regulatory cells capable of actively inhibiting effector T cell (Teff) responses (e.g., FoxP3$^+$ regulatory T cells (Treg) and myeloid-derived suppressor cells) (Shevach, 2009, Immunity 30: 636-645; Teicher, 2009, Biochem. Pharmacol. 77:1665-1673). With respect to the latter, the balance between regulatory and effector T cell activities within tumor beds has emerged as a critical determinant of the efficacy of anti-tumor immune responses (Yamaguchi and Sakaguchi, 2006, Semin Cancer Biol. 16:115-123; Miller et al., 2006, J. Immunol. 177:7398-7405; Gao et al., 2007, J. Clin. Oncol. 25:2586-2593; Bates et al., 2006, J. Clin. Oncol. 24: 5373-5380; Oble et al., 2009, Cancer. Immun 9:3). In turn, this insight beckons new cancer immunotherapeutic strategies designed to tip the Treg:Teff balance away from inhibition and towards activation.

An ideal therapeutic would in fact be one that could simultaneously inhibit Treg and activate Teff cells. In developing strategies for coordinate modulation of Treg and Teff cells, two costimulator receptors of the tumor necrosis family receptor (TNFR) superfamily are of special interest—GITR (glucocorticoid-induced TNFR family-related gene) and OX40. Each of these surface receptors is transiently up-regulated on activated Teff cells, and interestingly, each is also expressed constitutively on Treg cells, with further induction upon activation (Ishii et al., 2010, Adv. Immunol. 105:63-98; Nocentini et al., 2007, Eur. J. Immunol. 37:1165-1169). Furthermore, both GITR and OX40 promote CD4$^+$ and CD8$^+$ T cell survival, proliferation and effector functions and abrogate Treg cell suppressive effects (Shimizu et al., 2002, Nat. Immunol. 3:135-142; Piconese et al., 2008, J. Exp. Med. 205:825-839; Ji et al., 2004, J. Immunol. 172:5823-5827; Vu et al., 2007, Blood 110:2501-2510; Cohen et al., 2010, PLoS One 5:e10436; van Olffen et al., 2009, J. Immunol. 182:7490-7500). Hence, the triggering of either receptor should in principle allow simultaneous modulation of both T cell classes. While this dual Treg/Teff modulatory potential could theoretically explain, at least in part, the documented anti-tumor efficacy of agonistic therapeutic mAb directed at the GITR and OX40 receptors (Piconese et al., 2008, J. Exp. Med. 205: 825-839; Zhou et al., 2007, J. Immunol. 179:7365-7375; Ko et al., 2005, J. Exp. Med. 202:885-891; Burocchi et al., 2011, Eur. J. Immunol. 41:3615-3626; Kitamura et al., 2009, Int. J. Cancer 125:630-638), no studies to date have formally demonstrated this causal link. Another unexplored question is whether therapeutic synergies might be achieved by co-triggering the OX40 and GITR receptors, given that each manifests analogous effects on both Teff and Treg cells.

Thus, there is a need in the art for new cancer immunotherapeutic treatments based on the coordinate modulation of Treg and Teff cells. The present invention addresses this unmet need in the art.

BRIEF SUMMARY OF THE INVENTION

In one aspect, the invention provides a fusion protein comprising a first domain and a second domain, wherein the first domain comprises a binding moiety that binds to a first member from the tumor necrosis family receptor (TNFR) superfamily and the second domain comprises a binding moiety that binds to a second member from the TNFR superfamily.

In another aspect, the invention provides a method of regulating immune cells, comprising contacting a populating of immune cells with a fusion protein comprising a first domain and a second domain, wherein the first domain comprises a binding moiety that binds to a first member from the TNFR superfamily and wherein the second domain comprises a binding moiety that binds to a second member from the TNFR superfamily.

In yet another aspect, the invention provides a method of modulating an immune response in a mammal in need thereof, comprising administering to the mammal a therapeutically effective amount of a fusion protein comprising a first domain and a second domain, wherein the first domain comprises a binding moiety that binds to a first member from the TNFR superfamily and wherein the second domain comprises a binding moiety that binds to a second member from the TNFR superfamily.

In yet another aspect, the invention provides a method of treating or ameliorating cancer in a mammal in need thereof, comprising administering to the mammal a therapeutically effective amount of a fusion protein comprising a first domain and a second domain, wherein the first domain comprises a binding moiety that binds to a first member from the TNFR superfamily and the second domain comprises a binding moiety that binds to a second member from the TNFR superfamily.

In yet another aspect, the invention provides a method of enhancing an immune response in a mammal in need thereof, comprising administering to the mammal a therapeutically effective amount of a fusion protein comprising a first domain and a second domain, wherein the first domain comprises a binding moiety that binds to a first member from the TNFR superfamily and wherein the second domain comprises a binding moiety that binds to a second member from the TNFR superfamily.

In various embodiments of any of the above aspects or any other aspect of the invention delineated herein, the first member from the TNFR superfamily and the second member from the TNFR superfamily are co-expressed in a single cell. In certain embodiments of the aspects recited herein, the first member from the TNFR superfamily comprises glucocorticoid-induced TNFR family-related gene (GITR). In other embodiments of the aspects recited herein, the first member from the TNFR superfamily is glucocorticoid-induced TNFR family-related gene (GITR). In yet other embodiments of the aspects recited herein, the second member from the TNFR superfamily comprises OX40. In yet other embodiments of the aspects recited herein, the second member from the TNFR superfamily is OX40. In yet other embodiments of the aspects recited herein, the first member from the TNFR superfamily comprises GITR and the second member from the TNFR superfamily comprises OX40. In yet other embodiments of the aspects recited herein, the first member from the TNFR superfamily is GITR and the second member from the TNFR superfamily is OX40. In yet other embodiments of the aspects recited herein, the first domain comprises an antibody or fragment thereof that binds GITR. In yet other embodiments of the aspects recited herein, the second domain comprises at least a portion of the extracellular domain of OX40 ligand. In yet other embodiments of the aspects recited herein, the second domain comprises the extracellular domain of OX40 ligand.

In various embodiments of any of the above aspects or any other aspect of the invention delineated herein, the fusion protein is an antibody-ligand protein comprising the sequence of SEQ ID NO: 5. In certain embodiments of the aspects recited herein, the fusion protein is a type I-II protein fusion wherein the first domain comprises a component of a type I protein and wherein the second domain comprises a component of a type II protein, further wherein the type I protein is a protein having its amino terminus orientated extracellularly in the native protein and the type II is a protein having its carboxyl terminus orientated extracellularly in the native protein.

In various embodiments of any of the above aspects or any other aspect of the invention delineated herein, the population of immune cells comprises regulatory T (Treg) cells and effector T (Teff) cells. In certain embodiments of the aspects recited herein, the fusion protein attenuates Treg suppressive function. In other embodiments of the aspects recited herein, the fusion protein inhibits Treg generation. In yet other embodiments of the aspects recited herein, the fusion protein increases Teff cell proliferation, interleukin-2 production, and NF-κB signaling. In yet other embodiments of the aspects recited herein, the mammal is human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1B, depicts a schematic illustration of anti-GITR Ab•OX40L expression cassettes and corresponding fusion proteins. In FIG. 1A, Anti-GITR Ab•OX40L consists of a 3-polypeptide unit where the central polypeptide is made up of four tandemly-arrayed sequence elements comprising the VH and CH1 domains of the agonistic rat IgG2b anti-GITR mAb (hybridoma clone YGITR765), the hinge (H), $C_{H2}$ and $C_{H3}$ domains of aglycosyl human IgG1, a second hinge region and the extracellular domain of murine OX40L. The second polypeptide consists of the κ light chain of the same YGITR765 mAb ($V_\kappa$ and $C_\kappa$ domains). The third polypeptide consists of a strep (ST)-tagged derivative of murine OX40L's extracellular domain. In FIG. 1B, a proposed schematized model of fully-assembled anti-GITR Ab•OX40L features two Ab binding sites for GITR, an OX40L trimer at the opposite end for OX40 binding, and a human Fc ($hFc_{\gamma1}$) component in the middle. To generate agents for individually triggering GITR and OX40 receptors (anti-GITR•$hFc_{\gamma1}$ and $hFc_{\gamma1}$•OX40L, respectively), truncated expression constructs were made eliminating either the OX40 or GITR binding elements. Shown are proposed models of $hFc_{\gamma1}$•OX40L and anti-GITR•$hFc_{\gamma1}$ fusion protein derivatives. Human $Fc_{\gamma1}$ ($hFc_{\gamma1}$), a third fusion protein derivative, consists of sequence elements for the hinge, $C_{H2}$ and $C_{H3}$ domains of aglycosyl human IgG1 and a second hinge region.

FIG. 2, comprising

FIG. 3, comprising FIG. 3A: CD4$^+$ T cells purified from BALB/c splenocytes were cultured in vitro for 3 d in the presence of anti-CD3 (0.25 mg/ml), anti-CD28 (1 mg/ml), mitomycin-C treated APC and 20 µg/ml anti-GITR Ab•OX40L or control fusion protein (87 nM each). The data represent [$^3$H]thymidine incorporation during the final 18 h of culture. FIG. 3B: Purified CD4$^+$ T cells (5×10$^4$/well) cultured in 96-well U-bottom plates for 3 d in the presence of anti-CD3-coated microbeads (2×10$^5$/well) and anti-GITR Ab•OX40L or control fusion protein (87 nM). The data represent mouse IL-2 levels in culture supernatants determined by ELISA. FIG. 3C and FIG. 3D: CD4$^+$ T cells cultured as described in FIG. 3A in the presence of 1.25 µg/ml (5.4 nM) anti-GITR Ab•OX40L (T) and either purified mGITR•$hFc_{\gamma1}$, mOX40•$hFc_{\gamma1}$, or the two decoy receptors combined. The concentration of the added decoy receptors is indicated and the data represent [$^3$H]thymidine incorporation during the final 18 h of culture. Data are mean±SEM of 3-6 individual samples and are representative of two independent experiments. Significant difference (*, p<0.05) by two-sided Student's t test.

FIG. 5, comprising FIG. 5A: BALB/c splenocytes were sorted into $CD4^+CD25^+$ Treg cells and $CD4^+CD25^-$ T responder cells and each cultured in vitro at $5 \times 10^4$/well in a U-bottom 96-well plate for 3 d in the presence of anti-CD3 (0.25 mg/ml), anti-CD28 (1 mg/ml), mitomycin-C treated APC and 4 µg/ml anti-GITR Ab•OX40L or control fusion protein (17.3 nM each). The data represent [$^3$H]thymidine incorporation during the final 18 h of culture. Data are mean±SEM of 3 individual samples and are representative of two independent experiments. Significant difference (*, p<0.05) by two-sided Student's t test. FIG. 5B: Comparison of Treg suppressive activity in Treg plus T responder cell cultures where Treg were pre-treated with 20 µg/ml anti-GITR Ab•OX40L or control fusion protein (87 nM each) prior to culture addition and data are calculated as percent control suppression compared to untreated cultures. Results show the mean percent suppression calculated from eight individual cultures and error bars indicate the SEM.

FIG. 6, comprising FIG. 6A: Flow cytometric analysis of $CD4^+CD25^-$ T cells purified from BALB/c splenocytes and cultured in vitro for 3 d in the presence of anti-CD3 (1 µg/ml), anti-CD28 (2 µg/ml), TGFβ (5 ng/ml) and 20 µg/ml anti-GITR Ab•OX40L or control fusion protein (87 nM each). Histograms depict expression of CD25 and FoxP3 within the gated CD4-expressing cells. Histograms show only live cells based upon forward and side light scatter values and numbers in quadrants indicate the respective frequencies of cells present. FIG. 6B: Comparison of the frequency of CD25 and FoxP3 double-positive CD4 cells for each treatment, calculated as a percent inhibition compared to untreated cells. Results show the mean percent inhibition calculated from three independent flow cytometric experiments and bars indicate the SEM. Significant difference (*, p<0.01) by two-sided Student's t test.

FIG. 7, comprising FIG. 7A: BALB/c mice were inoculated s.c. with $1 \times 10^6$ CT26 cells, a syngeneic colon cancer cell line. Palpable tumors 3-5 mm in size received intratumoral injection of 25 µg of anti-GITR Ab•OX40L or control fusion protein (108 nM each) and fusion protein injections were repeated on alternating days for a total of 5 treatments (arrows). Tumor volume was determined by length×(width)$^2$/2 (in cubic millimeters). Each group consists of eight mice and lines represent tumor growth kinetics of individual mice. Data are representative of two independent experiments. FIG. 7B: Comparison of tumor size on day 10 post first treatment, subjected to statistical analysis. Significant difference (*, p<0.05) by two-sided Student's t test. FIG. 7C: Kaplan-Meier survival curve of BALB/c mice inoculated with CT26 cells and treated with fusion proteins, as shown in (FIG. 7A). FIG. 7D: Survival curve of BALB/c mice inoculated with $5 \times 10^5$ 4T1 cells, a breast cancer cell line, and treated with intratumoral injection of 25 µg of anti-GITR Ab•OX40L or control fusion protein (108 nM each) on day 6, 8, 10, 12 and 15 post tumor inoculation. Each group consisted of five mice. Comparison of two survival distributions was used to calculate significant difference.

FIG. 9, comprising FIG. 9A is a schematic diagram of the polypeptide expression cassettes of the six constructs generated for fusion protein assembly. Each expression cassette was subcloned into the pMF expression vector containing the elongation factor 1α promoter and the indicated antibiotic resistance gene. Abbreviations: SP, signal peptide; Vκ, variable region of kappa light chain; Cκ, constant region of kappa light chain; $V_H$ and $C\gamma_{2a}$, variable and constant regions of mAb heavy chain, respectively; $hC\gamma_1$, Fc region of human IgG1; H, hinge region of human IgG1; S-tag, Strep tag sequence; Neo, neomycin; Bla, blasticidin; and Zeo, zeocin. FIG. 9B depicts a chart and associated Coomassie blue-stained 10% reducing PAGE gel of Protein-A purified anti-GITR Ab•OX40L and control fusion proteins. The plus symbol indicates the composition of each fusion protein. Symbols and arrows indicate the electrophoretic position of each expressed polypeptide protein on the gel. The extra bands at approximately 50 and 25 kDa are bovine immunoglobulin heavy and light chains that co-purify with fusion proteins.

FIG. 10, comprising FIG. 10A is an image depicting serial dilutions of purified fusion proteins that were incubated with 293T cells ($1 \times 10^5$/sample) expressing mouse GITR receptor. Cells were washed and stained with a FITC-conjugated mAb against the Fc region of humanIgG1 or an isotype control and analyzed by flow cytometry. The mean fluorescence intensity (MFI) of each sample was calculated and plotted against protein concentration. FIG. B depicts the same analysis as in FIG. A except that the analysis was conducted with 293T cells expressing mouse OX40 receptor.

DETAILED DESCRIPTION OF THE INVENTION

Figure 1:
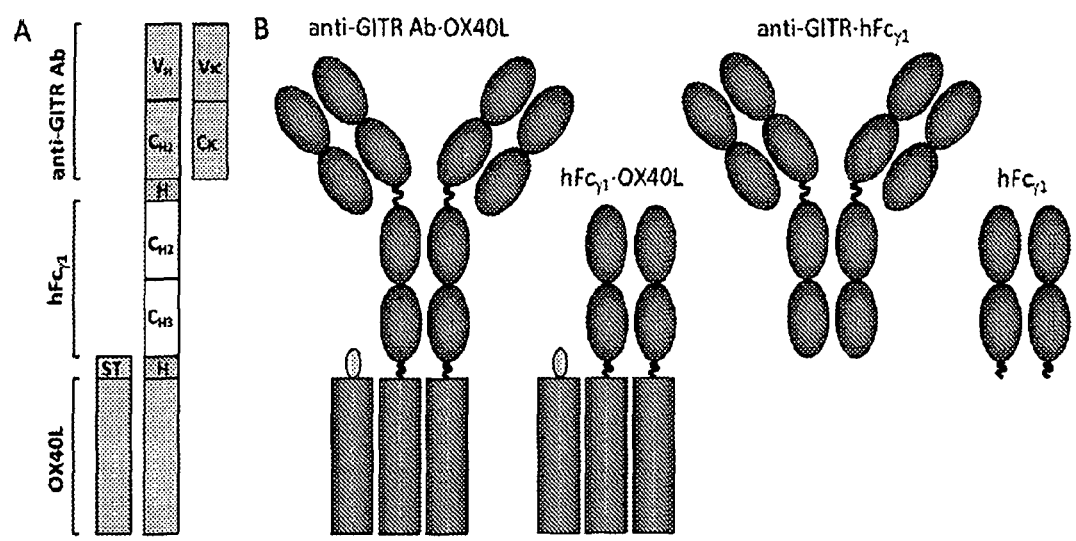
FIG. 1, comprising

The present invention provides compositions and methods for co-triggering desired receptors on a cell. In one embodiment, the receptors are co-triggered using soluble derivatives of their cognate ligands, which are added in combination with each other. In another embodiment, a chimeric or otherwise fusion protein designed to co-trigger the two desired receptors is used. As a non-limiting example, the results presented herein demonstrate that co-triggering of OX40 and GITR, whether using separate or fused together, leads to functional synergies, both in vitro and in vivo. In particular, in vitro analyses indicate that the fusion protein of the present invention is a cancer immunotherapeutic agent for coordinate Treg/Teff modulation.

The present invention relates generally to a fusion protein having a dual-signaling property referred elsewhere herein as a dual-signaling fusion protein. In one embodiment, the dual-signaling fusion protein of the invention is able to modulate regulatory T (Treg) cells and effector T (Teff) cells.

In one embodiment, the invention relates to a dual-signaling fusion protein that modulates at least two members of the tumor necrosis family (TNF) receptor superfamily. Preferably, the at least two members of the TNF receptor super family includes GITR and OX40.

In one embodiment, the present invention provides a fusion protein comprising a first domain and a second domain, wherein the first domain comprises an antigen binding site that targets GITR and the second domain comprises an antigen binding site that targets OX40. In one embodiment, the fusion protein of the invention modulates the activity of GITR and OX40.

In one embodiment, the present invention provides a fusion protein comprising a first domain and a second domain, wherein the first domain comprises a polypeptide component that targets GITR and the second domain comprises a polypeptide component that targets OX40. In one embodiment, the fusion protein of the invention modulates the activity of GITR and OX40.

In one embodiment, the present invention provides a fusion protein comprising a first domain and a second domain, wherein the first domain is a polypeptide that binds GITR and the second domain is a polypeptide that binds to OX40.

In one embodiment, co-triggering two receptors of the TNF receptor superfamily (e.g., GITR and OX40) inhibits Treg cells and activates Teff cells in parallel. This coordinate cellular modulatory capacity provides a new type of fusion protein immunoadjuvant that can be used with downstream therapeutic therapies in clinical contexts where immunopotentiation is desired, for example, cancer treatment and vaccination.

Accordingly, the fusion proteins of the invention may be employed in the treatment of disorders such as cancer and infectious diseases, for example, viral diseases.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "binding molecule" as used herein includes molecules that contain at least one antigen binding site that specifically binds to its target. For example, in one embodiment, a binding molecule for use in the methods of the invention comprises an immunoglobulin antigen binding site or the portion of a ligand molecule that is responsible for receptor binding.

As used herein, "biologically active or immunologically active" refers to fusion proteins according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild type proteins which are the building blocks of the fusion proteins of the present invention.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

By "chimeric protein" is meant any single polypeptide unit that comprises two distinct polypeptide domains, wherein the two domains are not naturally occurring within the same polypeptide unit. Typically, such chimeric proteins are made by expression of a cDNA construct but could be made by protein synthesis methods known in the art.

"Co-stimulatory ligand," as the term is used herein, includes a molecule on that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, GITR ligand, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, and the like. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, GITR, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation.

The term "derivative" as used herein in relation to the amino acid sequence means chemical modification of a fusion protein of the invention.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "effector cell" refers to a cell which mediates an immune response against an antigen. An example of an effector cell includes, but is not limited to, a T cell or a B cell.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fusion protein" refers to a protein comprising amino acid sequences of two or more different proteins.

The term "glucocorticoid-induced TNF receptor" (abbreviated herein as "GITR"), also known as TNF receptor superfamily 18 (TNFRSF18), TEASR, and 312C2, as used herein, refers to a member of the tumor necrosis factor/nerve growth factor receptor family. GITR is a 241 amino acid type I transmembrane protein characterized by three cysteine pseudorepeats in the extracellular domain and specifically protects T-cell receptor-induced apoptosis, although it does not protect cells from other apoptotic signals, including Fas triggering, dexamethasone treatment, or UV irradiation (Nocentini, G, et al. (1997) Proc. Natl. Acad. Sci., USA 94:6216-622). The nucleic acid and amino acid sequences of human GITR (hGITR), of which there are three splice variants, are known and can be found in, for example GenBank Accession Nos. gi:40354198, gi:23238190, gi:23238193, and gi:23238196.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells. Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like.

"Immune cell," as used herein includes any cell that is involved in the generation, regulation or effect of the acquired or innate immune system Immune cells include T cells such as CD4+ cells, CD8+ cells and various other T cell subsets, B cells, natural killer cells, macrophages, monocytes and dendritic cells, and neutrophils.

The term "immune related disease" means a disease in which a component of the immune system of a mammal causes, mediates or otherwise contributes to morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human.

"Negative signal", as used herein, means a signal that induces the typical cascade of intracellular events associated with among other things, decrease proliferation, decrease activation, decrease cellular processing, and the like.

"Positive signal," as used herein, means a signal that induces the typical cascade of intracellular events associated with among other things increase, proliferation, increase activation, increase cellular processing, and the like.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"OX40," as used herein refers to a member of the TNFR superfamily that is a polypeptide of 277 amino acids in length. The extracellular region is amino acids 29-214, with amino acids 31-166 of this being the TNFR homology region, with three CRDs. The structure and some critical binding sites of OX40 and OX40 ligand have been determined. Compaan, D. et al., "The crystal structure of the Costimulatory OX40-OX40L complex", Structure 14: 1321-1330 (2006), incorporated herein by reference. The CRDs of OX40 appear to be important for receptor binding of the OX40 ligand, including CRD1, aa 30-65; CRD2, aa 67-81 and CRD3, aa 109-125. OX40 has been sequenced in a number of different species, including, but not limited to, mouse: Swiss Prot. Accession No. P47741: human: Swiss Prot. Accession No. P43489; and rat: Swiss Prot. Accession No. 15725.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "regulatory T cell" or "Treg cell" refers to a naturally occurring subtype of T cell that can inhibit T-cell immune responses to an antigen. Treg cells represent a distinct T-cell lineage that has a key role in an individual's tolerance of self-antigens and the prevention of autoimmune disease and inappropriate immune responses. When activated, they are anergic and suppress the proliferation and cytokine production of conventional T cells. Like all T cells, Treg cells require T cell receptor activation and costimulation to become fully active.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

The term "subject" is intended to include living organisms in which an immune response can be elicited (e.g., mammals).

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the term "variant" means any polypeptide having a substitution of, deletion of or addition of one (or more) amino acid from or to the sequence (or any combination of these), including allelic variations, as compared with the wild-type protein, so long as the resultant variant fusion protein retains at least 75%, 80%, 85%, 90%, 95%, 99% or more of the biological or immunologic activity as compared to the wild-type proteins as used in the present invention.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the discovery that a fusion protein that binds to at least two members from the tumor necrosis family receptor (TNFR) superfamily can modulate both regulatory T (Treg) and effector T (Teff) cells. In one embodiment, the at least two members of the TNFR superfamily includes glucocorticoid-induced TNFR family-related gene (GITR) and OX40. Accordingly, the invention provides methods of using the fusion proteins of the invention to modulate GITR and OX40 in treating various disorders such as cancer and infectious diseases, for example, viral diseases.

In one embodiment, the invention provides compositions and methods for increasing Teff cell proliferation, interleukin-2 production, and NF-κB signaling.

In another embodiment, the invention provides compositions and methods for attenuating Treg suppressive function and suppressing Treg generation.

Compositions

In one embodiment, the present invention provides a fusion protein comprising a first domain and a second domain, wherein the first domain comprises a binding moiety that binds to a member from the Tumor Necrosis Factor Receptor (TNFR) superfamily and the second domain comprises a binding moiety that binds to a member from the TNRF superfamily.

TNF/TNFR generally refers to any member of either the Tumor Necrosis Factor (TNF) superfamily or the Tumor Necrosis Factor Receptor (TNFR) superfamily. The TNF superfamily includes, for example, CD40 ligand, OX40 ligand, 4-1BB ligand, CD27, CD30 ligand (CD153), TNF-α, TNF-β, RANK ligand, LT-α, LT-β, GITR ligand, and LIGHT. The TNFR superfamily includes, for example, CD40, OX40, 4-1BB, CD70 (CD27 ligand), CD30, TNFR2, RANK, LT-βR, HVEM, GITR, TROY, and RELT. However, the invention should not be limited to these members. Rather, the invention includes any member from the TNF/TNFR superfamily.

TNF/TNFR generally refers to any member of either the Tumor Necrosis Factor (TNF) superfamily or the Tumor Necrosis Factor Receptor (TNFR) superfamily. In humans, currently 19 TNF superfamily and 28 TNFR superfamily members have been identified (Table 1).

TABLE 1

| TNF superfamily ligand | TNFR superfamily |
|---|---|
| TNFα | TNF-R1 |
| LTα | TNF-R2 |
| LTβ | LTβR |
| LIGHT | HVEM |
|  | DcR3 |
| FasL | Fas |
| TL1A | DR3 |
| RANKL | RANK |
| TRAIL | TRAIL-R1 (DR5) |
|  | TRAIL-R2 (DR5) |
|  | TRAIL-R3 (DcR1) |
|  | TRAIL-R4 (DcR2) |
| TWEAK | Fn14 |
|  | DR6 |
| CD40L | CD40 |
| OX40L | OX40 |
| GITRL | GITR |
| CD30L | CD30 |
| CD27L | CD27 |
| 4-1BBL | 4-1BB |
| EDA-A1 | EDAR |
| EDA-A2 | XEDAR |
|  | TROY |
| APRIL | TACI |
| BAFF | BCMA |
|  | BAFF-R |
| NGF | NGFR |

In one embodiment, the first member from the TNFR superfamily is GITR and the second member from the TNFR superfamily is OX40.

In one embodiment, the fusion protein of the invention comprises a first domain and a second domain, wherein the first domain comprises a polypeptide component that binds to a first member from the TNFR superfamily and the second domain comprises a polypeptide component that binds to a second member from the TNFR superfamily.

In one embodiment, the invention provides a fusion protein comprising a first domain and a second domain, wherein the first domain comprises a polypeptide component that binds to GITR and the second domain comprises a polypeptide component that binds to OX40.

In one embodiment, the fusion protein of the invention acts on the OX40 and GITR signaling pathway. For example, a fusion protein having a first domain that comprises a polypeptide that binds to GITR and a second domain that comprises a polypeptide that binds to OX40 can simultaneously trigger signaling associated with GITR and OX40 on a cell. In particular, the first domain is a polypeptide that has the capacity to bind with GITR to trigger a GITR specific signal on a cell bearing GITR, and the second domain is a polypeptide that has the capacity to bind with OX40 to trigger an OX40 signal on a cell bearing OX40.

In one embodiment, the domain in the fusion protein of the invention that comprises a binding moiety that binds GITR acts as a GITR agonist. That is, GITR binding moieties useful for binding GITR on a cell include binding molecules that specifically bind to GITR and act as a GITR agonist.

In one embodiment, the domain in the fusion protein of the invention that comprises a binding moiety that binds OX40 acts as an OX40 agonist. That is, OX40 binding moieties useful for binding OX40 on a cell include binding molecules that specifically bind to OX40 and act as an OX40 agonist.

Accordingly, the invention includes a fusion protein comprising a first domain and a second domain, wherein the first domain comprises an agonist to a first member from TNFR superfamily and the second domain comprises an agonist to a second member from the TNFR superfamily.

TNFR agonist or TNF/TNFR agonist referred herein includes any suitable agonist of any member of either the TNF superfamily or the TNFR superfamily. In many cases, a member of one superfamily can be an agonist of a complementary member of the other superfamily. For example, OX40 ligand (a member of the TNF superfamily) can act as an agonist of OX40 (a member of the TNFR superfamily), and OX40 can act as an agonist of OX40 ligand. Thus, suitable TNFR agonists include, for example, CD40 ligand, OX40 ligand, 4-1BB ligand, CD27, CD30 ligand (CD153), TNF-α, TNF-β, RANK ligand, LT-α, LT-β, GITR ligand, LIGHT, CD40, OX40, 4-1BB, CD70 (CD27 ligand), CD30, TNFR2, RANK, LT-βR, HVEM, GITR, TROY, and RELT. Additionally, suitable TNF/TNFR agonists include certain agonistic antibodies raised against a complementary member of the other TNF/TNFR superfamily.

One skilled in the art armed with the specification would understand that any combination of TNFR agonists that achieves the dual Teff activation/Treg inhibition effect is encompassed in the invention. The desired dual effect of the TNFR agonist combination can be tested using methods disclosed herein or methods known in the art.

In one embodiment, the fusion protein of the invention creates an auto-signaling/bi-directional signaling loop on a single cell. Without wishing to be bound by any particular theory, it is believed that the auto-signaling/bi-directional signaling loop on a single cell leads to a greater signaling efficacy because the dual signaling component of the fusion protein is co-localized on the cell.

In another embodiment, the fusion protein of the invention can bridge cells together. Without wishing to be bound by any particular theory, where two fusion proteins of the invention are side-by-side but in opposite directions, the fusion proteins of the invention can bridge cells together.
Antibody In one embodiment, the fusion protein of the invention comprises a binding moiety that specifically binds to its target. For example, in one embodiment, the binding moiety comprises an antibody or fragment thereof comprising an antigen binding site. Preferably, the antibody is an agonist to the target.

By way of a non-limiting example, the GITR binding domain in the fusion protein of the invention is an anti-GITR antibody. Various forms of anti-GITR antibodies can be made using standard recombinant DNA techniques (Winter and Milstein, Nature, 349, pp. 293-99 (1991)). Therefore, the anti-GITR portion of the fusion protein of the invention exhibits an "agonist" property on a cell bearing GITR.

An agonist in the broadest sense includes any molecule that partially or fully enhances, stimulates or activates one or more biological activities of a corresponding target (e.g., GITR) in vitro, in situ, or in vivo. Examples of such biological activities of GITR include promoting CD4+ and CD8+ T cell survival, proliferation and effector functions and abrogate Treg cell suppressive effects or the generation of Treg cells. An agonist may function in a direct or indirect manner. For instance, the agonist may function to partially or fully enhance, stimulate or activate one or more biological activities of GITR in vitro, in situ, or in vivo as a result of its direct binding to GITR, which causes receptor activation or signal transduction.

Generally, the binding moiety includes, an antibody (including full length), a monoclonal antibody (including full-length monoclonal antibody), a polyclonal antibody, a multispecific antibody (e.g., bispecific antibody), human, humanized or chimeric antibody, antibody fragment, e.g., Fab fragments, F(ab') fragment, fragment produced by a Fab expression library, epitope-binding fragment of any of the above, and engineered forms of antibodies (i.e., molecules comprising binding sites derived from antibody molecules), e.g., scFv molecules or molecules comprising scFv molecule, so long as they exhibit the desired activity.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and gem-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-GITR antibodies directed against the human GITR antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human gem-line immunoglobulin gene array in gem-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

In some embodiments, the antibody is humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the present invention, the ability to bind for example human GITR. However, using certain methods of humanization, the affinity and/or specificity of binding of the antibody for human GITR may be increased using methods of "directed evolution," as described by Wu et al., J. Mol. Biol., 294:151 (1999), the contents of which are incorporated herein by reference herein in their entirety.

In one embodiment, the antigen binding moiety is characterized by particular functional features or properties of an antibody. For example, the antigen binding moiety binds specifically GITR, preferably human GITR. In one embodiment, the invention relates to an antigen binding moiety comprising an antibody or functional fragment thereof, wherein the antibody specifically binds to a GITR protein or fragment thereof.

In one embodiment, the antibody fragment provided herein is a single chain variable fragment (scFv). In another embodiment, the antibodies of the invention may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)). In one embodiment, the antibodies and fragments thereof of the invention binds a GITR protein with normal or enhanced affinity.

In one embodiment, an antibody of the invention comprises heavy and light chain variable regions comprising amino acid sequences that are homologous to the amino acid sequences of the preferred antibodies described herein, and wherein the antibodies retain the desired functional properties of the anti-GITR antibodies of the invention.

In some embodiments, the antibody of the invention is further prepared using an antibody having one or more of the VH and/or VL sequences disclosed herein can be used as starting material to engineer a modified antibody, which modified antibody may have altered properties as compared to the starting antibody. In various embodiments, the antibody is engineered by modifying one or more amino acids within one or both variable regions (i.e., VH and/or VL), for example within one or more CDR regions and/or within one or more framework regions. Additionally or alternatively, an antibody is engineered by modifying residues within the constant region(s), for example to alter the effector function(s) of the antibody.

In one embodiment, the present invention comprises an anti-GITR/OX40 fusion protein. In another embodiment, the term "anti-GITR/OX40 fusion protein" refers to the specific fusion protein comprising SEQ ID NO: 5.

However, the invention should not be limited to a fusion protein comprising a domain that targets GITR, wherein the domain comprises an antibody directed against GITR. Rather, the fusion protein of the invention can be engineered to comprise any GITR binding agent. A GITR binding agent includes, but is not limited to, GITR ligand or soluble extracellular ligand domains thereof, anti-GITR antibodies, and immunologically effective portions of anti-GITR antibodies so long as they exhibit the desired activity.

In one embodiment, the fusion protein of the invention is generated by combining a type I protein (i.e., amino terminus is extracellular in the native protein) with a type II membrane protein (i.e., carboxyl terminus is extracellular in the native protein). In this configuration, the respective functional ends of the fusion protein are not buried internally where the components are linked. For example, the antibody (e.g., anti-GITR Ab) component of the fusion protein is paired with the ligand (e.g., OX40L) component of the fusion protein.

Ligand

In one embodiment, the fusion protein of the invention comprises a binding moiety that specifically binds to its target. For example, in one embodiment, the binding moiety comprises a domain that is responsible for receptor binding.

Preferably, the domain that is responsible for receptor binding is a ligand or fragment thereof. More preferably, the ligand or fragment thereof is an agonist to the corresponding receptor.

By way of a non-limiting example, the domain in the fusion protein of the invention that comprises a ligand or fragment thereof is OX40L. Various forms of OX40L can be made using standard recombinant DNA techniques. Therefore, the OX40L portion of the fusion protein of the invention exhibits an "agonist" property on a cell bearing OX40.

An agonist in the broadest sense includes any molecule that partially or fully enhances, stimulates or activates one or more biological activities of a corresponding target (e.g., OX40) in vitro, in situ, or in vivo. Examples of such biological activities of OX40 include promoting CD4+ and CD8+ T cell survival, proliferation and effector functions and abrogate Treg cell suppressive effects. An agonist may function in a direct or indirect manner. For instance, the agonist may function to partially or fully enhance, stimulate or activate one or more biological activities of OX40 in vitro, in situ, or in vivo as a result of its direct binding to OX40, which causes receptor activation or signal transduction.

OX40L specifically binds to the OX40 receptor. The human protein is described in PCT Publication No. WO 95/21915. The mouse OX40L is described in U.S. Pat. No. 5,457,035. The naturally occurring OX40 ligand includes intracellular, transmembrane and extracellular domains. A functionally active soluble form of OX-40 ligand ("soluble OX-40 ligand") can be produced by deleting the intracellular and transmembrane domains as described, e.g., in U.S. Pat. Nos. 5,457,035 and 6,312,700, and WO 95/21915, the disclosures of which are incorporated herein for all purposes. A functionally active form of OX-40 ligand is a form that retains the capacity to bind specifically to the OX-40 receptor, that is, that possesses an OX-40 "receptor binding domain." Methods of determining the ability of an OX-40 ligand molecule or derivative to bind specifically to the OX-40 receptor are discussed elsewhere herein. Methods of making and using the OX-40 ligand and its derivatives (such as derivatives that include an OX-40 receptor binding domain) are described in WO 95/21915 (supra), which also describes proteins comprising the soluble form of OX-40 ligand linked to other peptides, such as human immunoglobulin ("Ig") Fc regions, that can be produced to facilitate purification of OX-40 ligand from cultured cells, or to enhance the stability of the molecule after in vivo administration to a mammal (see also, U.S. Pat. No. 5,457,035).

As used herein, the term "OX-40L" includes the entire OX-40 ligand, soluble OX-40 ligand, and functionally active portions of the OX-40 ligand. Also included within the definition of OX-40L are OX-40 ligand variants which vary in amino acid sequence from naturally occurring OX-40 ligand molecules but which retain the ability to specifically bind to an OX-40 receptor. Such variants are described in U.S. Pat. No. 5,457,035 and WO 95/21915 (supra).

Generally, the fusion protein of the invention can be engineered to comprise any OX40 binding agent. An OX40 binding agent includes, but is not limited to, OX40L or soluble extracellular ligand domains thereof, anti-OX40 antibodies (for example, monoclonal antibodies such as humanized monoclonal antibodies), and immunologically effective portions of anti-OX40 antibodies so long as they exhibit the desired activity.

In one embodiment, the fusion protein of the invention is generated by combining a type I protein (i.e., amino terminus is extracellular in the native protein) with a type II membrane protein (i.e., carboxyl terminus is extracellular in the native protein). In this configuration, the respective functional ends of the fusion protein are not buried internally where the components are linked. For example, the antibody (e.g., anti-GITR Ab) component of the fusion protein is paired with the ligand (e.g., OX40L) component of the fusion protein.

Genetic Modification

The invention relates to a dual-signaling fusion protein that modulates at least two members of the TNF receptor superfamily. Preferably, the at least two members of the TNF receptor super family includes GITR and OX40. As a non-limiting example, the invention includes an anti-GITR/OX40L fusion protein and related fusion proteins. The invention also encompasses variants of the fusion proteins. While in general it is desirable for variants to show enhanced ability for binding to a given molecule, in some embodiments variants may be designed with slightly reduced activity as compared to other fusion proteins of the invention, for example, in instances in which one would purposefully want to attenuate activity. Variants or derivatives can be generated that would have altered multimerization properties. When engineering variants, this could be done for example, for either the entire extracellular domain of the desired TNF or TNFR superfamily, or for that component of the extracellular domain that is incorporated within the fusion protein itself.

Preferably, variants or derivatives of the fusion proteins of the present invention maintain the hydrophobicity/hydrophilicity of the amino acid sequence.

The invention also provides chemical modification of a fusion protein of the invention. Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a fusion protein conjugated with polyethylene glycol (PEG), or addition of PEG during chemical synthesis of a polypeptide of the invention. Modifications of polypeptides or portions thereof can also include reduction/alkylation; chemical coupling to an appropriate carrier or mild formalin treatment.

Other derivatives of the fusion proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylation site(s) are added or glycosylation sites are deleted or disabled. Furthermore, if no glycosylation is desired, the proteins can be produced in a prokaryotic host expression system.

Variants and/or derivatives of the fusion proteins of the invention can be prepared by chemical synthesis or by using site-directed mutagenesis [Gillman et al., Gene 8:81 (1979); Roberts et al., Nature 328:731 (1987) or Innis (Ed.), 1990, PCR Protocols: A Guide to Methods and Applications, Academic Press, New York, N.Y.] or the polymerase chain reaction method [PCR; Saiki et al., Science 239:487 (1988)], as exemplified by Daugherty et al. [Nucleic Acids Res. 19:2471 (1991)] to modify nucleic acids encoding the complete receptors.

The fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath J (1992) Protein Expr Purif 3-0.26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and anti-GITR/OX40L is useful to facilitate purification.

Additional fusion expression vectors include pGEX (Pharmaci, a Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used. In addition, retroviral and lentiviral expression vectors can also be used. Furthermore, any one of a number of in vivo expression systems designed for high level expression of recombinant proteins within organisms can be invoked for producing the fusion proteins specified herein.

In another embodiment a fusion protein of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products).

In order to enhance stability and/or reactivity, the fusion proteins of the present invention can also be modified to incorporate one or more polymorphisms in the amino acid sequence resulting from natural allelic variation. Additionally, D-amino acids, non-natural amino acids or non-amino acid analogues can be substituted or added to produce a modified fusion protein within the scope of this invention.

The amino acid sequences of the present invention may be produced by expression of a nucleotide sequence coding for same in a suitable expression system.

In brief summary, the expression of natural or synthetic nucleic acids of the invention is typically achieved by operably linking a nucleic acid encoding the desired polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

In addition, or in the alternative, the fusion protein itself can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic polypeptides may be confirmed by amino acid analysis or sequencing (e.g., the Edman degradation procedure). Additionally, the amino acid sequence of a fusion protein of the invention, or any part thereof, may be altered during direct synthesis and/or combined using chemical methods with a sequence from other subunits, or any part thereof, to produce a variant polypeptide.

Assays for measuring the immunologic activity of any homolog, derivative or variant of any fusion protein of the present invention are well known in the art.

For example, any one of several conventional assays for monitoring cytokine production, as a measure of immune cells activation and differentiation, can be invoked. For example, for tracking T cell activation, interleukin-2 can be employed as a marker, which can be assayed as described in Proc. Natl. Acad. Sci. USA. 86:1333 (1989) the pertinent portions of which are incorporated herein by reference. A kit for an assay for the production of interferon is also available from Genzyme Corporation (Cambridge, Mass.). One can also employ immunofluorescence and flow cytometry to monitor cytokine production on a cellular basis, and to monitor cell surface markers that reflect cellular activation and/or differentiation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Another assay for monitoring T cell proliferation is based on loading T cells with the CFSE dye, and subsequently monitoring by flow cytometry the dilution of this dye that accompanies successive cell divisions. In addition to monitoring T cell proliferation, the bioactivity of the fusion protein of the invention can also be monitored by evaluating its capacity to inhibit the suppressive activity of CD4+ CD25+Treg cells, suppresses CD25+Foxp3+ Treg conversion, enhance anti-tumor immunity, and the like.

The bioactivity of the fusion protein of the invention can also be monitored by evaluating whether costimulation with combined signals, such as GITR and OX40 signals, promote immune responses by (i) conferring resistance to Treg suppression (ii) inhibiting Treg suppressive activity, and (iii) inhibiting Treg induction.

The bioactivity of the fusion protein of the invention can also be monitored by evaluating whether costimulation with combined signals, such as GITR and OX40 signals increase the number and/or killing function of tumor antigen-specific Teff cells involved in tumor regression.

Methods

The invention provides methods for attenuating Treg activity as well as stimulating T effector cell (Teff) activity. Accordingly, the fusion proteins of the invention have a wide therapeutic applicability in the treatment of a variety of diseases by modulating immune responses. In addition the fusion proteins agents can be used in conjunction with vaccines to enhance the immune response.

In one embodiment, the fusion proteins of the invention can be used to increase Teff cell proliferation, interleukin-2 production, and NF-κB signaling. Preferably, the fusion protein of the invention allows for dual signaling to at least two members of the tumor necrosis family receptor (TNFR) superfamily (e.g., GITR and OX40). For example, the dual signaling fusion protein of the invention that targets GITR and OX40 provides a significantly greater effect on Teff compared to if GITR and OX40 receptors were stimulated individually.

In one embodiment, the fusion proteins of the invention can be used to attenuate Treg suppressive function and inhibit their generation via TGF-β induction. For example, the dual signaling fusion protein of the invention that targets GITR and OX40 provides a significantly greater effect on Treg compared to if GITR and OX40 receptors were stimulated individually.

In one embodiment, the fusion proteins of the invention can be used as an anti-cancer agent because as demonstrated elsewhere herein, co-engagement of GITR and OX40 receptors using the fusion protein of the invention slows tumor growth and significantly enhances survival compared to engaging the receptors individually. In one embodiment, the fusion proteins of the invention can be used to enhance cytotoxicity of CD8+ T cells.

The present invention is also directed to methods for treating a patient for an illness comprising administering to the patient an effective amount of a fusion protein of the present invention. Various illnesses can be treated according to the present methods, including but not limited to cancer, such as ovarian carcinoma, breast carcinoma, colon carcinoma, glioblastoma multiforme, prostate carcinoma, and leukemia; viral infections, such as chronic viral infections with HBV, HCV, HTLV-1, HTLV-II, EBV, HSV-I, HSV-II, and KSHV; and bone marrow myelodysplastic syndromes.

Examples of cancer include but are not limited to, carcinoma, lymphoma, blastoma, sarcoma, and leukemia or lymphoid malignancies. More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulvar cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia, chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

In the context of treatment for cancer, the fusion proteins of the present invention can optionally be administered to a patient in combination with other chemotherapeutic agents. Suitable chemotherapeutic agents include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins, capecitabine; and pharmaceutically acceptable salts, acids or derivatives of any of the above.

Additional information on the methods of cancer treatment is provided in U.S. Pat. No. 7,285,522, incorporated by reference in its entirety.

Dosage and Formulation (Pharmaceutical Compositions)

Administration of the therapeutic composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Fusion Protein-Mediated Co-Triggering of the GITR and OX40 Receptors Differentially Regulates Regulatory and Effector T Cells T cell-centered cancer immunotherapeutic strategies have been geared towards enhancing effector T (Teff) cell responses or inhibiting the regulatory T (Treg) cells that can suppress these responses. Two members of the TNF receptor family, GITR and OX40, have each been attributed abilities to augment and inhibit Teff and Treg cells, respectively. The experiments disclosed herein relates to the consequences of co-triggering these receptors with a dual-signaling fusion protein, anti-GITR Ab•OX40L. Assessing anti-GITR Ab•OX40L function in vitro, with anti-CD3/CD28 mAb-activated mouse $CD4^+$ T cells as responders, it has been established that this fusion protein increases Teff proliferation, interleukin-2 production, and NF-κB signaling to a significantly greater extent than do triggers of GITR and OX40 receptors when deployed individually. Turning to CD4⁺CD25⁺ Treg cells, anti-GITR Ab•OX40L attenuates Treg suppressive function and inhibits their generation via TGF-β induction significantly more than its component ligands, added alone or in combination. In tumor-bearing BALB/c mice, intra-tumoral co-engagement of GITR and OX40 receptors, whether with combined or fused triggers, slowed tumor growth and significantly enhanced survival compared to engaging the receptors individually. Notably, CD8⁺ T cells from anti-GITR Ab•OX40L-treated mice exhibit greater cytotoxic activity than those from mice treated with individual or combined triggers. The results presented herein demonstrate that dual-signaling fusion proteins, and combinatorial therapeutics more generally, can offer substantial advantages over single-function agents for immunomodulation.

The materials and methods employed in these experiments are now described.

Methods and Materials

Cell Lines, Mice, and Tumor Models

The CT26 and 4T1 tumor cell lines were purchased from ATCC (Manassas, Va.) and cultured in RPMI-1640 media with 10% fetal bovine serum. Line CT26 is a N-nitroso-N-methylurethane induced colon carcinoma cell line from BALB/c mice. Line 4T1 is a thioguanine-resistant metastatic variant of 410.4, a spontaneously arising mammary tumor from BALB/cfC3H mice (Aslakson and Miller, 1992, Cancer Res. 52:1399-1405). BALB/c mice were purchased from The Jackson Laboratory (Bar Harbor, Me.) and used at 6-12 weeks of age. Animal care protocols were approved by the Institutional Animal Care and Use Committee of Thomas Jefferson University. To establish tumors, CT26 cells ($1\times10^6$) or 4T1 ($5\times10^5$) were resuspended in PBS and inoculated subcutaneously (s.c.) into the shaved flank of BALB/c mice. Tumor diameter was measured by electronic caliper every 2-3 d, measuring length and width at their longest points, and tumor volume was determined by length×(width)²/2. Tumors measuring 3-5 mm in diameter each received an intratumoral injection of 108 nM of anti-GITR Ab•OX40L (25 μg) or control fusion protein and fusion protein injections were repeated on alternating days for a total of 5 treatments. Surviving mice tumor free after 5 weeks were re-challenged with tumor cells ($1\times10^6$) injected s.c. in the opposite flank to insure tumor regression was mediated by anti-tumor immune responses.

The 293T cell line, a highly transfectable derivative of the HEK293 cell line expressing SV40 T antigen, was purchased from ATCC and cultured in DMEM with 10% fetal bovine serum (FBS). The Chinese hamster ovary (CHO)-S cell line was purchased from Invitrogen and cultured in DMEM/F-12 with 10% FBS. To generate transfectants expressing GITR and/or OX40, sequences encoding full-length mouse GITR or OX40 were cloned into pMFzeo and pMFneo (Tone et al., 2008, Nat. Immunol. 9:194-202), respectively, and then transfected into 293T cells selected with zeocin and/or G418 antibiotics.

Fusion Protein Generation and Production

In preparation for vector construction, variable heavy and light chain sequences of a commercially-available agonistic anti-mouse GITR mAb, hybridoma clone YGITR765 (rat IgG2b, κ), were reverse transcribed using GeneRacer (Invitrogen) from hybridoma RNA and PCR amplified using GeneRacer 5' forward primers and 5'-ACAACACACGR-GACCTTAGGAG-3' (SEQ ID NO: 1) and 5'-CACTCAT-TCCTGTTGAAGCTC-3' (SEQ ID NO: 2), respectively, as reverse primers (Ponte et al., 2010, Immunology 130:231-242). PCR products for the variable heavy and light chain genes were subcloned and confirmed by sequencing. The fusion protein anti-GITR Ab•OX40L consists of a 3-polypeptide unit (FIG. 1).

Figure 9A:
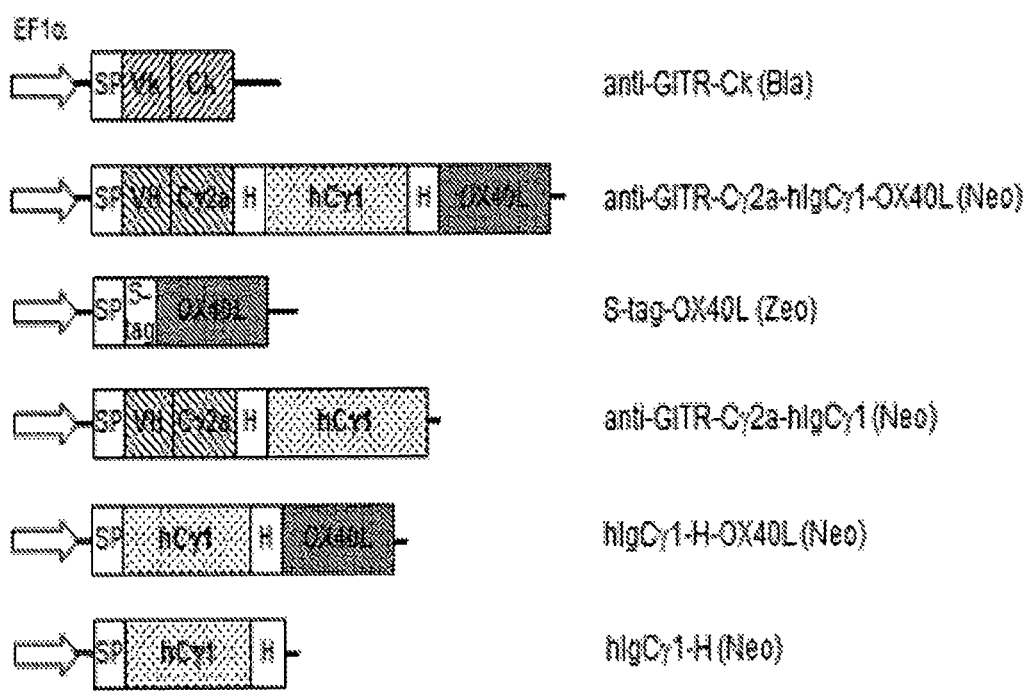
FIGS. 9A-9B, is a series of images depicting the generation of chimeric anti-GITR Ab•OX40L and control fusion proteins.

The central polypeptide of this unit is composed of fused sequence elements beginning with the $V_H$ and $C_{H1}$ domains of anti-GITR mAb, the hinge region of human IgG1 (EPK-SCDKTHTCPPCP; SEQ ID NO: 3), the $C_{H2}$ and $C_{H3}$ domains of aglycosyl human IgG1, a second IgG1 hinge region, and the extracellular domain of murine OX40L (amino acids 50-198), arrayed sequentially (FIG. 9A). The chimeric sequence encoding the full-length fusion protein was then sub-cloned into the mammalian expression vector pMFneo, enabling G418 selection.

The second construct consists of the cDNA sequence encoding the κ light chain of the same YGITR765 mAb ($V_\kappa$ and $C_\kappa$ domains) cloned into pMFblas, enabling blasticidin selection.

Figure 9B:
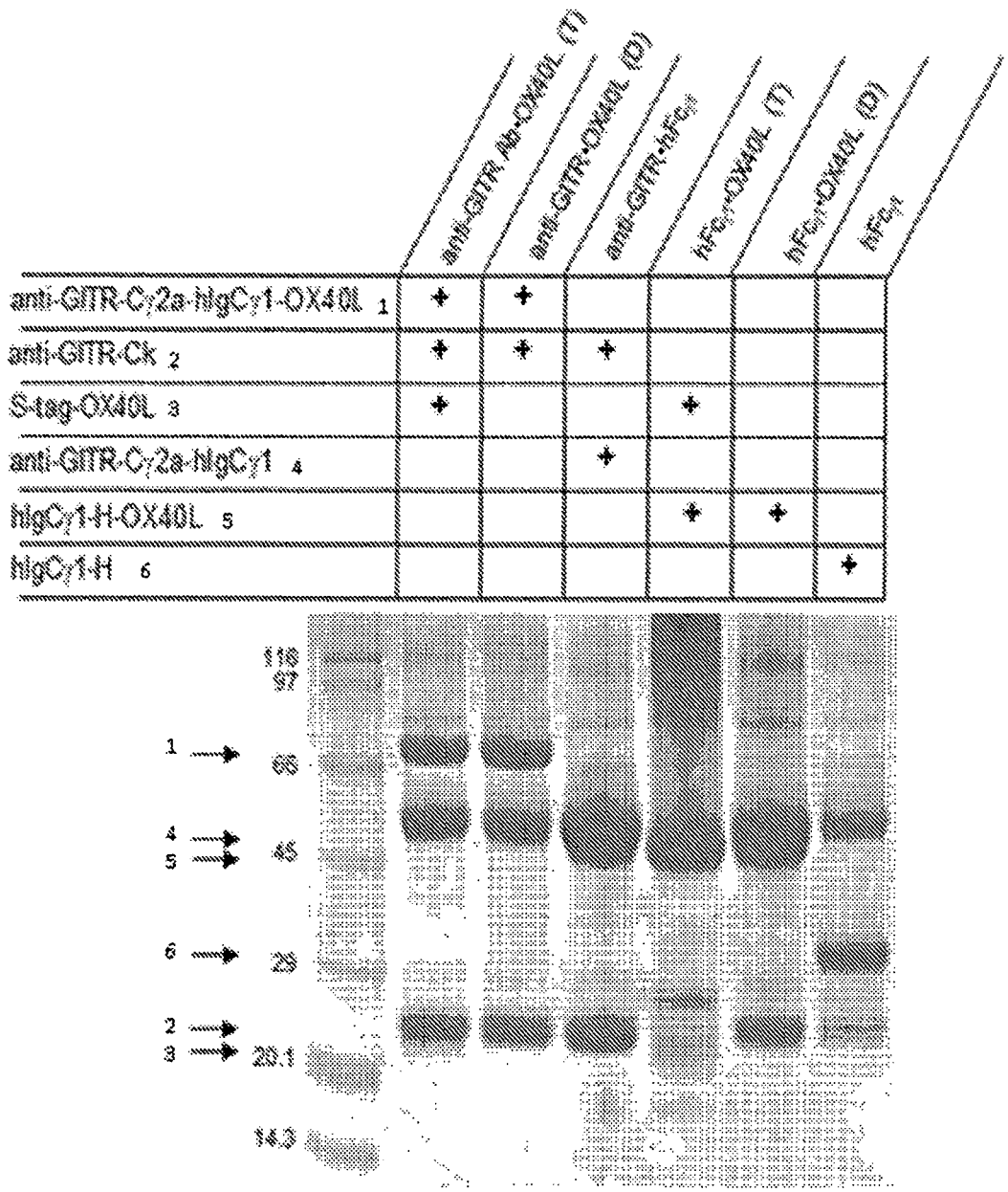

The third construct consists of fused sequence elements encoding an eight amino acid strep-tag (WSHPQFEK; SEQ ID NO: 4), a human IgG1 hinge region, and murine OX40L's extracellular domain cloned into pMFzeo, enabling zeocin selection. To generate this 3-polypeptide unit, CHO-S cells were co-transfected with each expression plasmid for their respective units and selected for stable transfectants using a combination of G418 (Mediatech, Inc.), blasticidin and zeocin (Invitrogen) antibiotics. Fusion protein was purified from culture supernatants using protein A agarose beads (FIG. 9B). Agents were also produced for individually triggering GITR and OX40 receptors, namely, anti-GITR•hFc$_{\gamma1}$ and hFc$_{\gamma1}$•OX40L (FIG. 1B). Human Fc$_{\gamma1}$ (hFc$_{\gamma1}$), a third fusion protein derivative, was produced to control for Fc functional activity. Mouse (m) GITR•hFc$_{\gamma1}$ and mOX40•hFc$_{\gamma1}$ decoy fusion proteins are composed of the extracellular domains of mouse GITR (aa 20-152) and mouse OX40 (aa 20-211), respectively, fused to the hinge, $C_{H2}$ and $C_{H3}$ domains of aglycosyl human IgG1 and subcloned into pMFneo.

Cognate Receptor Binding Analysis

Expression of mouse GITR or OX40 on the surface of 293T cells transfected with mGITR/pMFzeo or mOX40/pMFneo, respectively, was confirmed by surface staining and immunofluorescence. Increasing amounts of anti-GITR Ab•OX40L(T) or anti-GITR Ab•OX40L(D) fusion proteins were incubated for 1 h with GITR/293T transfectants, then washed, surface stained with FITC-conjugated anti-human IgG1 (Fc specific) mAb (Jackson Immunoresearch) and analyzed by flow cytometry, determining the mean fluorescence intensity (MFI) for each sample. To measure anti-GITR Ab•OX40L, hFc$_{\gamma1}$•OX40L(T) or hFc$_{\gamma1}$•OX40L(D) binding to OX40 expressing 293T cells, fusion proteins were incubated with OX40/293T transfectants and analyzed in the same manner.

NF-κB Luciferase Reporter Assay

To detect NF-κB activity in 293T cells expressing mouse GITR and OX40 on their surface, pNF-κB-Luc (Clontech) plasmid (5 μg) and phRL-TK (Promega) plasmid (2 μg) were co-transfected into $1\times10^7$ GITR+OX40/293T cells by Gene Pulser Xcell (BioRad). 5 h after electroporation, cells were cultured with anti-GITR Ab•OX40L fusion protein or component ends at two concentrations (5.4 and 10.8 nM) for 24 h. Cells were harvested and the promoter activity was measured using the Dual Luciferase Reporter (Promega) assay system, normalizing firefly luciferase (pNF-κB-Luc) to the *Renilla* luciferase internal control (phRL-TK).

T Cell Proliferation Assays

CD4+ T cells and CD8+ T cells were isolated from the spleens of female BALB/c mice, 8-10 weeks of age, by negative selection using subset specific isolation kits (Miltenyi Biotec). APCs were isolated from BALB/c splenocytes using CD11b Microbeads (Miltenyi). Purified T cells ($2 \times 10^5$ cells/well) were cultured with soluble anti-CD3 (145-2C11, 0.25 µg/ml)/anti-CD28 (37.51, 1 µg/ml) mAbs and mitomycin C-treated APC ($6 \times 10^5$ cells/well) in the presence of anti-GITR Ab•OX40L or component end fusion proteins for 3 d at 37° C. For the final 18 h of culture, 0.5 µCi [methyl-3H]thymidine/well was added and the incorporated radioactivity was measured using a microbeta plate counter (Wallac). Data were collected as the mean CPM of 3-6 individual assays. For competition studies, mGITR•hFc$_{\gamma 1}$ and mOX40•hFc$_{\gamma 1}$ decoy receptors were added to the cultures (at the indicated concentration) at the same time as fusion protein addition. To measure IL-2 production by T cells, purified CD4+ T cells ($2 \times 10^5$ cells/well) were cultured for 48 h in triplicate in round-bottom 96-well plates with fusion proteins and protein A agarose beads ($2 \times 10^5$ beads/well) coated with anti-CD3 mAb. Supernatants were collected and IL-2 levels determined by a Ready-Set-Go ELISA (eBioscience).

T Cell Suppression Assay

CD4+CD25+ and CD4+CD25− T cell subsets were purified from spleen and lymph node cells by cell sorting (BD Aria). Purity of these populations was typically 97% or greater. CD4+CD25+ T cells ($5 \times 10^4$/well) were co-cultured with CD4+CD25− T cells ($5 \times 10^4$/well) in the presence of T cell-depleted γ-irradiated splenocytes as APC ($1.5 \times 10^5$/well), 25 ng/ml anti-CD3 (145-2C11) mAb and 1 µg/ml anti-CD28 (37.51) mAb in 96-well round-bottom plates. Each culture, set-up in triplicate, was pulsed with 0.5 µCi of [$^3$H]thymidine for the final 18 h of a 72 h incubation. For pre-treatment studies, purified CD4+CD25+ T cells were pre-incubated with fusion protein at 20 µg/ml (87 nM) for 2 hours, washed 3 times with media, and added to co-cultures of CD4+CD25− T cells, as described herein.

In Vitro Generation of CD25+Foxp3+ Regulatory T Cells

CD25+CD4− T cells were purified from BALB/c splenocytes by cell sorting (BD Aria) and analyzed for purity by flow cytometry (>97%). To induce Treg conversion, CD25+ CD4− cells ($5 \times 10^4$/well) were cultured for 72 h in 96-well plates with plate-bound anti-CD3 (1 µg/ml) and soluble anti-CD28 (2 µg/ml) mAb in the presence of 5 ng/ml TGF-β1 (Peprotech). Fusion protein was added to the cultures as indicated. Cells were harvested for flow cytometry and stained with fluorochrome-conjugated anti-CD4, anti-CD25 and anti-Foxp3 mAb (permeabilized to detect intracellular expression; eBioscience), counting the number of CD25+, Foxp3+ double-positive cells within the CD4+ gated population.

Cytotoxicity Assays

To quantify target-cell killing activity mediated by tumor specific T lymphocytes, lactate dehydrogenase (LDH) enzyme released from CT26 target cells was measured following an established method (Konjevic et al., 1997, J. Immunol. Methods 200:199-201). CT26 tumors were generated in BALB/c mice and treated by intratumoral injection of fusion protein, as described herein. On day 10, after the initial treatment, anti-CD8 microbeads (Miltenyi Biotec) were used to purify CD8+ T cells from the spleen and draining lymph nodes of tumor-bearing mice treated with anti-GITR Ab•OX40L or anti-GITR•hFc$_{\gamma 1}$ and hFc$_{\gamma 1}$•OX40L fusion proteins. These CD8+ effector cells were incubated for 4 h in 96 well round bottom plates with CT26 target cells ($5 \times 10^3$/well) at different effector:target ratios. To control for spontaneous LDH release, additional wells were set up containing effectors cells only, target cells only, target cell maximal release, and media only. A cytotoxity detection kit (Roche) measuring LDH released into supernatants was used, following the manufacturer's instructions. Using the LDH OD values, and subtracting for media alone, the formula for calculating percent CTL cytotoxicity is: [(experimental, effector+ target release)−(effector spontaneous release)−(target spontaneous release)]/[(target maximal release)−(target spontaneous release)]×100.

Statistical Analysis

Data are expressed as mean±SEM. Analyses were performed using Prism software (GraphPad Software, Inc.). The difference between the mean of two groups were considered significant when p<0.05.

The results of the experiments are now described.

Generation of Chimeric Anti-GITR Ab•OX40L

Individually, costimulation through either the GITR or OX40 receptors has been shown to enhance T cell-mediated anti-tumor immunity (Piconese et al., 2008, J. Exp. Med. 205:825-839; Zhou et al., 2007, J. Immunol. 179:7365-7375; Kitamura et al., 2009, Int. J. Cancer 125:630-638; Burocchi et al., 2011, Eur. J. Immunol. 41:3615-3626; Ramirez-Montagut et al., 2006, J. Immunol. 176:6434-6442). However, the possibility that co-triggering of these receptors might yield functional synergies has not been explored. A chimeric dual-signaling protein for co-triggering of these receptors was designed. First, in contrast to co-administered cognate ligands for GITR and OX40, a fusion protein incorporating triggers for both receptors could favor simultaneous engagement of the cognate receptors adjacent to each other on the same cell, in a bridging fashion. Second, invoking a fusion protein for co-triggering serves to membrane-anchor each of the triggers, with the consequent potential for higher functional affinity.

Specifically, the fusion protein anti-GITR Ab•OX40L was generated, which combines an agonistic Ab component for GITR triggering together with a derivative of OX40L's extracellular domain for OX40 triggering. The decision to use an Ab as one of the fusion protein components was driven by the fact that native GITR ligand (GITRL) and OX40L are both type II membrane proteins, making chimerization of their respective extracellular domains problematic. An Ab•ligand fusion provides for a convenient type I-II protein fusion. Anti-GITR Ab•OX40L consists of a 3-polypeptide unit, schematized in FIG. 1A. The central polypeptide of this unit consists of four tandemly-arrayed sequence elements: the V$_H$ and C$_{H1}$ domains of the agonistic rat IgG2b anti-GITR mAb (hybridoma clone YGITR765), the hinge, C$_{H2}$ and C$_{H3}$ domains of aglycosyl human IgG1, a second hinge region, and the extracellular domain of murine OX40L. The second polypeptide consists of the κ light chain of the same YGITR765 mAb (V$_\kappa$ and C$_\kappa$ domains). The third polypeptide consists of a strep-tagged derivative of murine OX40L's extracellular domain. The 3-polypeptide unit, once fully-assembled, features: (i) two Ab binding sites for GITR, (ii) an OX40L trimer at the opposite end, and (iii) a human Fc (hFc) component in the middle, allowing for efficient purification by protein-A chromatography (FIG. 1B). To generate this 3-polypeptide unit, expression plasmids for the respective units were co-transfected into CHO cells, each carrying a distinct antibiotic-resistance gene that together allowed for selection of all three.

A representative sequence of the polypeptide units of the fusion protein is as follows:

DTA-1 Heavy Chain-human IgG-mouse OX40L
(SEQ ID NO: 5)
MEFGLSWVFLVAILKGVQCEVQLVESGGGLAEPGRSLRLACTASGFTFG

NYAITWFRQAPGKGLEWVAFIRSKIYHAASDHAASVKGRFTISRDDSNG

VAYLQMNSLQTEDTAVYYCSRAALYDYGDYGDFDYWGHGTLVTVSSAST

KGPSVFPLAPSSKSTSGGTAALGCLVKDYFPEPVTVSWNSGALTSGVHT

FPAVLQSSGLYS

LSSVVTVPSSSLGTQTYICNVNHKPSNTKVDKKV-

EPKSCDKTHTCPPCP-

APELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCS

VMHEALHNHYT

QKSLSLSPGK-

EPKSCDKTHTCPPCP-

QLSSSPAKDPPIQRLRGAVTRCEDGQLFISSYKNEYQTMEVQNNSVVIK

CDGLYIIYLKGSFFQEVKIDLHFREDHNPISIPMLNDGRRIVFTVVASL

AFKDKVYLTVNAPDTLCEHLQINDGELIVVQLTPGYCAPEGSYHSTVNQ

VPL, wherein the amino acid sequence comprises, respectively, as illustrated above, $V_H$ and $C_{H1}$ domains of anti-GITR mAb, the hinge region of human IgG1 (EPKSCDKTHTCP-PCP; SEQ ID NO: 3), the $C_{H2}$ and $C_{H3}$ domains of aglycosyl human IgG1, a second IgG1 hinge region, and the extracellular domain of murine OX40L.

DTA-1 Light Chain
(SEQ ID NO: 6)
MGLSWVFLVALLKGIQCEVQLVETGGGLVRPGSSLKLSCATSGFTFSN

TWMNWVRQAPGKGLEWVALIKEKYTNYEAKYAESVKGRFTISRDDSKS

RVYLQMNTLRDQDTATYYCTVQLGPFDYWGQGVTVTVSSAQTTAPSVY

PLAPGCGDTTSSTVTLGCLVKGYFPEPVTVTWNSGALSSDVHTFPAVL

QSGLYTLTSSVTSSTWPSQTVTCNVAHPASSTKVDKKVGS

STREP-tag-mouse OX40L
(SEQ ID NO: 7)
WSHPQFEK-

QLSSSPAKDPPIQRLRGAVTRCEDGQLFISSYKNEYQTMEVQNNSVVI

KCDGLYIIYLKGSFFQEVKIDLHFREDHNPISIPMLNDGRRIVFTVVA

SLAFKDKVYLTVNAPDTLCEHLQINDGELIVVQLTPGYCAPEGSYHST

VNQVPL wherein the amino acid sequence comprises, respectively, as illustrated above, the eight amino acid strep-tag (SEQ ID NO: 4), a human IgG1 hinge region, and murine OX40L's extracellular domain Agents for individually triggering GITR and OX40 receptors were also produced, namely, anti-GITR•$hFc_{\gamma 1}$ and $hFc_{\gamma 1}$•OX40L (FIG. 1B). Human $Fc_{\gamma 1}$ ($hFc_{\gamma 1}$), a third fusion protein derivative, was produced to control for Fc functional activity. Further details dealing with construct structure and assembly for the various recombinant proteins used in these experiments is set forth in FIG. 9. In each case, the molecular mass of the individual recombinant proteins, when analyzed on SDS-PAGE, was consistent with its predicted size.

Native OX40L, the ligand for OX40, is comprised of three identical subunits, although functional dimeric variants of OX40L have been reported (Sadun et al., 2008, J. Immunother. 31:235-245; Zubairi et al., 2004, Eur. J. Immunol. 34:1433-1440). For the experiments in this study, two types of anti-GITR Ab•OX40L-expressing CHO cell transfectants were generated, designated (D) for dimer and (T) for trimer. Anti-GITR Ab•OX40L (D) transfectants bear only two coding sequences: (i) the central polypeptide unit linking anti-GITR mAb heavy chain, $hFc_{\gamma 1}$ and OX40L sequences, and (ii) anti-GITR mAb light chain. Anti-GITR Ab•OX40L (T) transfectants include the third polypeptide expressing strep-tag OX40L. The anti-GITR Ab•OX40L (D) transfectants contain exclusively dimeric OX40L (along with dimeric Ig heavy/light chain at the other end of the fusion protein). By contrast, anti-GITR Ab•OX40L (T) transfectants have the potential to produce a mixture of both dimeric and trimeric OX40L derivatives. The presence of the trimeric variant was substantiated using a sandwich ELISA in which an anti-human Fc mAb is used as capture Ab and anti-strep-tag mAb is used as detecting Ab. However, attempts to purify trimeric anti-GITR Ab•OX40L using anti-strep-tag affinity chromatography gave low yields. Therefore, experiments here were performed using protein A-purified fusion proteins that in the case of anti-GITR Ab•OX40L (T) transfectants contain a mixture of dimer and trimer. A set of dimeric and trimeric $hFc_{\gamma 1}$•OX40L fusion proteins were produced using this same strategy, and in the case of $hFc_{\gamma 1}$•OX40L (T), are also a mixture of dimers and trimers.

Figure 10A:
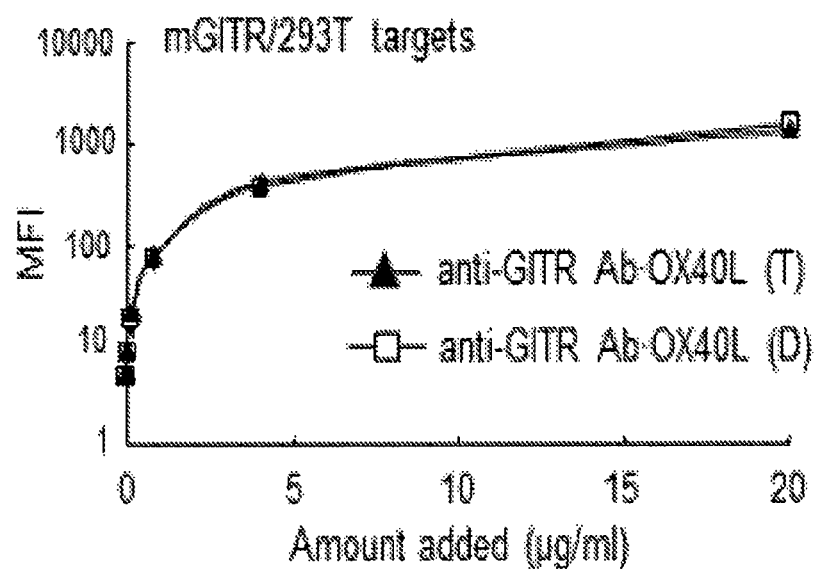
FIGS. 10A-10B, is a series of imaged demonstrating flow cytometric comparison of fusion protein binding to cognate receptors.
Figure 10B:
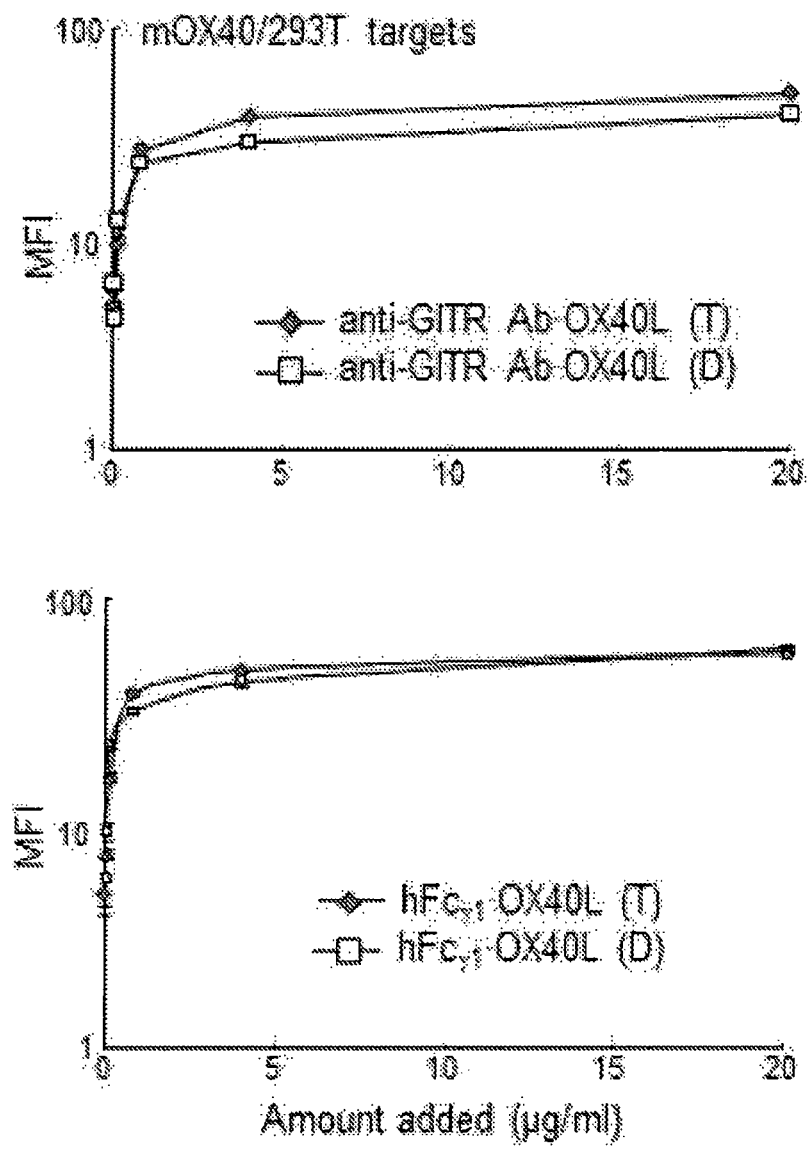

As a first functional validation of the trimeric and dimeric anti-GITR Ab•OX40L variants, it was demonstrated by immunofluorescence and flow cytometry that they bound to 293T transfectants with enforced expression of either of the cognate receptors (GITR or OX40) (FIG. 10). Based upon comparative mean fluorescence intensity (MFI) values, the trimeric and dimeric variants exhibited comparable, concentration-dependent binding to each of the single receptor-expressing transfectants Importantly, plots of MFI versus protein concentration indicated that anti-GITR Ab•OX40L has similar OX40 and GITR binding profiles to soluble $hFc_{\gamma 1}$•OX40L (FIG. 10) and anti-GITR•$hFc_{\gamma 1}$, respectively. This provides assurance that chimerization does not significantly disrupt receptor-binding potential.

Anti-GITR Ab•OX40L Provides Costimulatory Signals for T Cell Proliferation

Figure 2A:
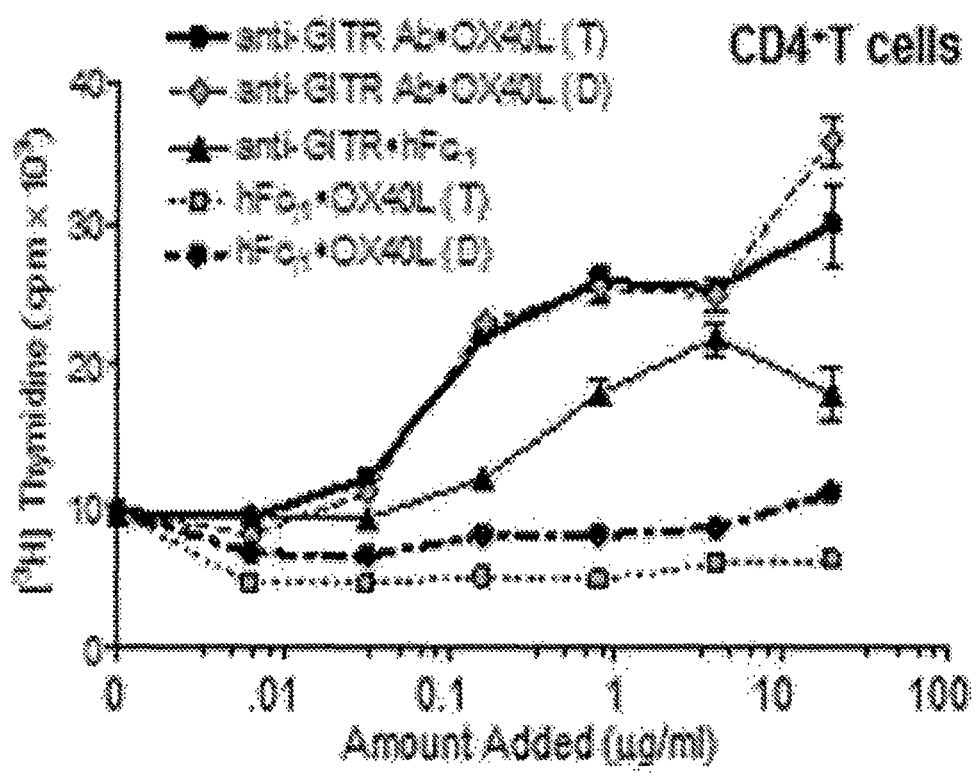
FIGS. 2A-2B, depicts a graph indicating that the treatment of CD4$^+$ and CD8$^+$ T cells with anti-GITR Ab•OX40L fusion protein enhances their proliferation. Purified CD4$^+$ (FIG. 2A) and CD8$^+$ (FIG. 2B) T cells isolated from the spleen of naïve BALB/c mice were cultured in vitro for 3 d in the presence of anti-CD3 mAb (0.25 µg/ml), anti-CD28 mAb (1 µg/ml), mitomycin C-treated APC, and serial dilutions (6.4-20,000 ng/ml) of anti-GITR Ab•OX40L (T) or (D), fusion protein component ends, or no protein. Data represent [methyl-3H]thymidine (0.5 µCi/well) incorporation during the final 18 h of culture. Dimeric (D) fusion proteins are derived from CHO-S transfectants that do not co-express the (ST)-tagged OX40L polypeptide unit. No significant difference was observed in anti-GITR Ab•OX40L and $hFc_{\gamma1}$•OX40L (T) vs. (D) treated samples. Data in FIG. 2A and FIG. 2B are mean±SEM of 6 individual samples and are representative of two independent experiments.

Several TNF receptor family members, including GITR and OX40, are expressed at high levels on activated CD4+ T cell surfaces (Watts, 2005, Annu. Rev. Immunol. 23:23-68). Triggering of either one delivers a potent costimulatory signal, leading to increased proliferation, cytokine production or memory cell generation (Nocentini and Riccardi, 2009, Adv. Exp. Med. Biol. 647:156-173; Prell et al., 2003, J. Immunol. 171:5997-6005). Therefore, functional analyses were performed by assessing fusion protein costimulation of naïve CD4+ T cells activated with low-dose anti-CD3/anti-CD28 mAb and mitomycin C-treated APC, used in part to anchor Fc fusion proteins (FIG. 2A). Costimulatory triggering of OX40 alone with $hFc_{\gamma 1}$•OX40L had little effect on proliferation, whereas triggering of GITR alone with anti-GITR•hFc enhanced proliferation in a dose-dependent fashion. Purified fusion protein products derived from anti-GITR Ab•OX40L (T) and (D) transfectants were equally effective at costimulating $CD4^+$ T cell proliferation, and yielded greater proliferation than anti-GITR•hFc$_{\gamma 1}$ alone (FIG. 2A). A control hFc$_{\gamma 1}$ protein derivative induced no increase in proliferation above the basal levels seen with paired anti-CD3/anti-CD28 mAb, ruling out the possibility that the hFc components of anti-GITR•hFc$_{\gamma 1}$ and anti-GITR Ab•OX40L are themselves responsible for the observed enhancement of $CD4^+$ T cell proliferation.

Figure 2B:
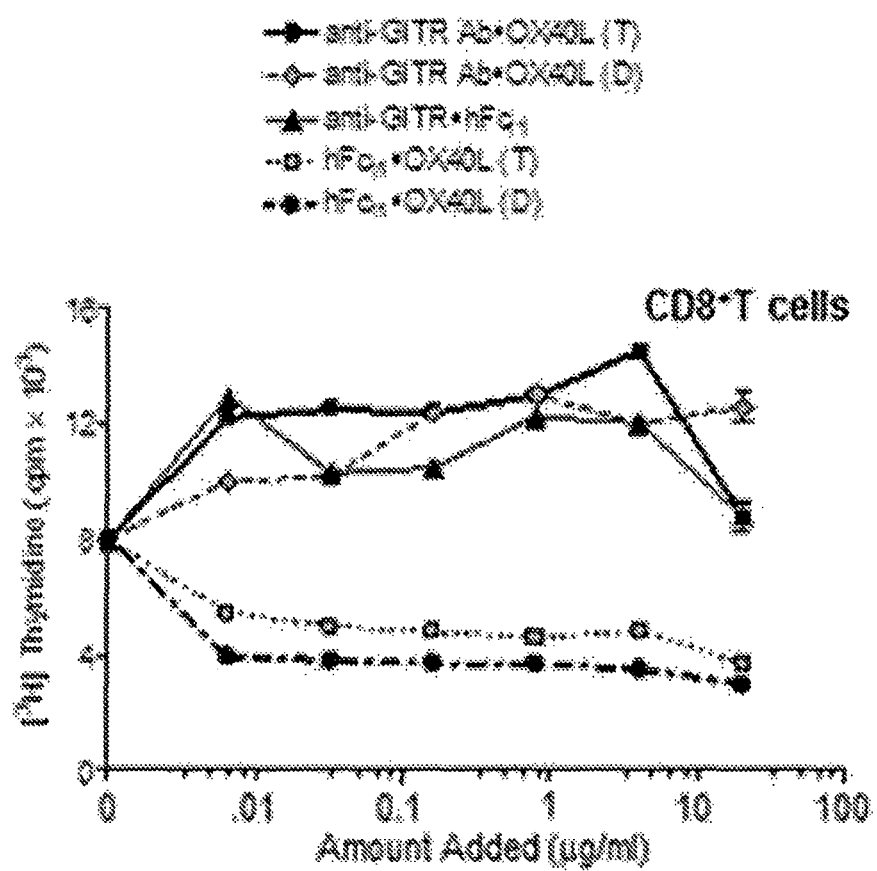

In a parallel set of experiments, anti-GITR Ab•OX40L and anti-GITR•hFc$_{\gamma 1}$ each increased $CD8^+$ T cell proliferation when compared to non-treated controls, albeit with dose-dependence apparent at only the lower concentrations (FIG. 2B). hFc$_{\gamma 1}$•OX40L did not costimulate $CD8^+$ T cells, and in fact appeared to inhibit proliferation. The observation that anti-GITR Ab•OX40L and anti-GITR•hFc$_{\gamma 1}$ exhibit similar potency for $CD8^+$ T cell proliferation suggests that co-triggering of GITR and OX40 receptors by anti-GITR Ab•OX40L may overcome inhibitory effects associated with isolated OX40 signaling. As before, no significant differences between fusion proteins produced by dimeric or trimeric transfectants in terms of their effects on $CD8^+$ T cell proliferation was observed.

Figure 3A:
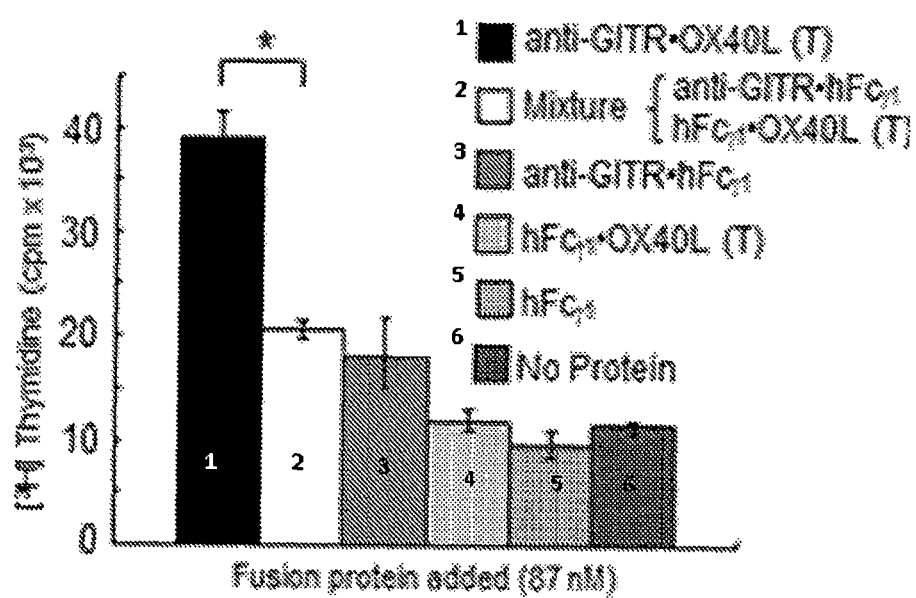
FIGS. 3A-3D, depicts bar graphs indicating that anti-GITR Ab•OX40L provides costimulation for CD4+ T cell proliferation and IL-2 production and its activity requires both ends of the fusion protein.

Co-Triggering of GITR and OX40 Receptors with a Dual-Signaling Fusion Protein Increases $CD4^+$ T Cell Proliferation More than its Components, Alone or in Combination Next, the relative functional activity of anti-GITR Ab•OX40L was compared to its components (anti-GITR•hFc$_{\gamma 1}$ and hFc$_{\gamma 1}$•OX40L), in the context as single agents alone or in combination. Combining anti-GITR•hFc$_{\gamma 1}$ and hFc$_{\gamma 1}$•OX40L as an equimolar mixture increased $CD4^+$ T cell proliferation above basal levels induced by anti-CD3/anti-CD28 mAbs (FIG. 3A), but not significantly more than anti-GITR•hFc$_{\gamma 1}$ alone, suggesting there was no functional advantage in this setting. Conversely, anti-GITR Ab•OX40L (T), with the capacity to co-trigger adjacent GITR and OX40 receptors on the same cell, induced nearly 2-fold more $CD4^+$ T cell proliferation than a combination of anti-GITR•hFc$_{\gamma 1}$ and hFc$_{\gamma 1}$•OX40L (T), even when each component was used at the same molar concentration as the fusion protein (FIG. 3A). First, this finding argues against the possibility that individual fusion protein components are separately triggering the OX40 and GITR receptors on the same T cell. Second, hFc$_{\gamma 1}$•OX40L (T) alone had no costimulatory activity, and yet when paired with anti-GITR triggering as part of an anti-GITR Ab•OX40L fusion protein, the combined signaling is much more potent than anti-GITR•hFc$_{\gamma 1}$ costimulation alone. This latter finding implies that (i) membrane anchoring of ligands, achieved through adjacent receptor bridging, enhances signaling effects, and/or (ii) when co-triggering occurs on the same T cell surface, combined OX40 and GITR signaling substantially improves the proliferative response.

Figure 3B:
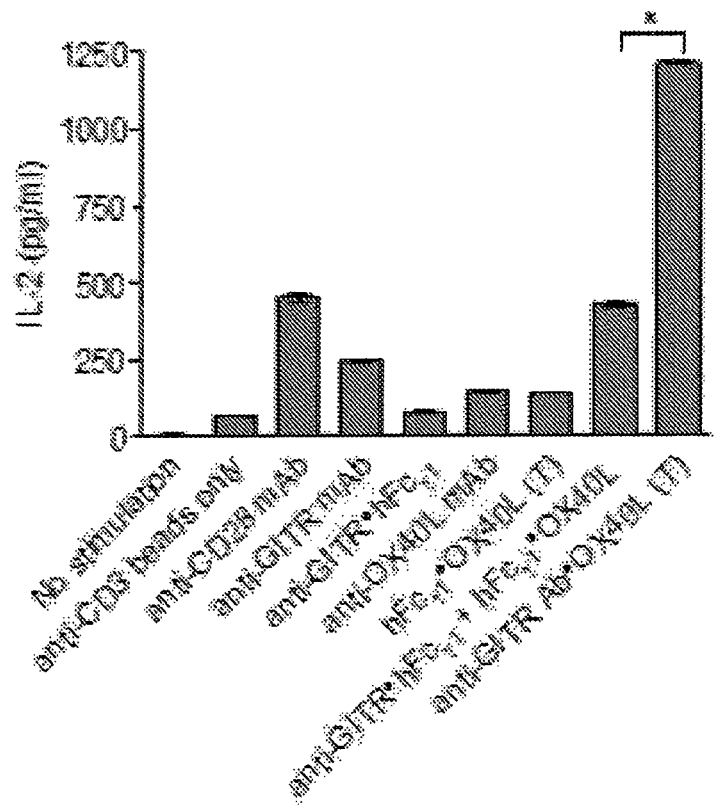

IL-2 production is critical for T cell clonal expansion and memory, while limited amounts of IL-2 favor Treg cell functions and immune tolerance (Shevach, 2009, Immunity 30: 636-645; Thornton et al., 2004, J. Immunol. 172:6519-6523; Malek and Castro, 2010, Immunity 33:153-165). Therefore, to help determine the mechanism of enhanced T cell proliferation induced by anti-GITR Ab•OX40L versus its components (anti-GITR•hFc$_{\gamma 1}$/hFc$_{\gamma 1}$•OX40L), IL-2 levels in $CD4^+$T cell cultures activated by anti-CD3 mAb-coated microbeads were measured. Cultures costimulated with anti-GITR Ab•OX40L contained 5-fold more IL-2 than those activated with anti-GITR mAb (DTA-1), anti-GITR•hFc$_{\gamma 1}$ or hFc$_{\gamma 1}$•OX40L and 2-fold more than anti-CD28 mAb at 1 µg/ml (FIG. 3B). Importantly, T cell cultures costimulated with anti-GITR Ab•OX40L (T) contained nearly 3-fold more IL-2 than those with combined anti-GITR•hFc$_{\gamma 1}$ and hFc$_{\gamma 1}$•OX40L. Thus, potential bridging of GITR and OX40 receptors on T cell surfaces with anti-GITR Ab•OX40L is a potent driver of IL-2 production, and the higher IL-2 levels may be contributing to the previously observed increase in T cell proliferation.

Figure 3C:
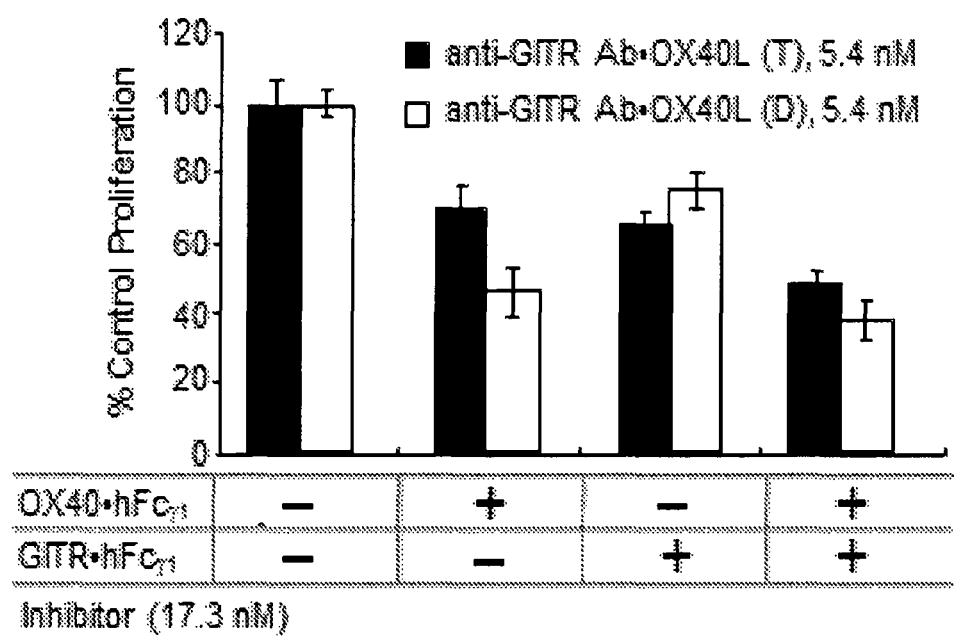
Figure 3D:
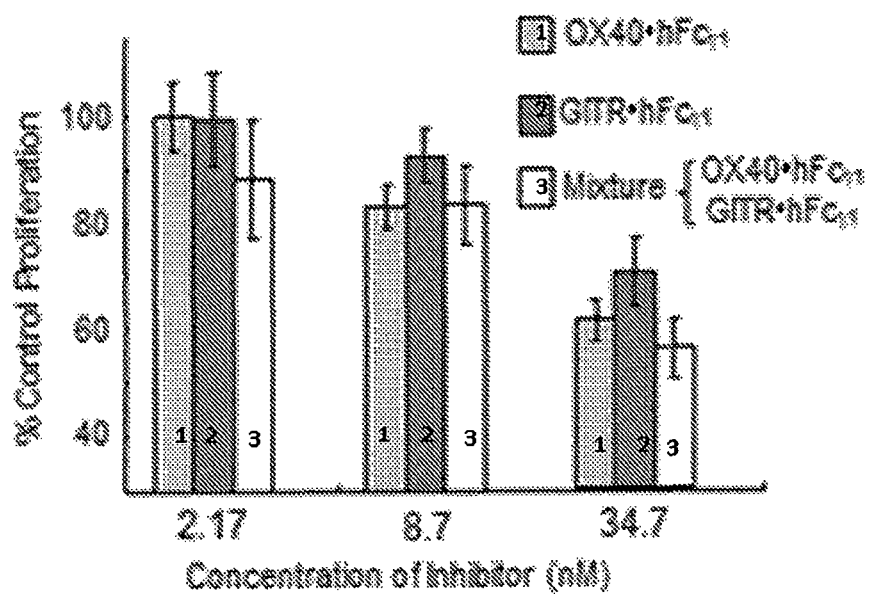

To further document the functional contribution of both ends of the fusion protein in proliferation assays, decoy receptors as blocking agents was used. To this end, two decoy receptors were invoked, mGITR•hFc$_{\gamma 1}$ and mOX40•hFc$_{\gamma 1}$, which interfere with OX40L:OX40 and GITRL:GITR interactions, respectively (Nocentini et al., 2007, Ann. N. Y. Acad. Sci. 1107:380-391; Burgess et al., 2004, J. Allergy Clin. Immunol. 113:683-689). Each decoy receptor abrogated anti-GITR Ab•OX40L-driven stimulation of $CD4^+$T cell proliferation, and as a mixture, the combined decoy receptors were even more effective (FIG. 3C). Furthermore, the inhibitory effect of these decoy receptors on $CD4^+$T cell proliferation was dose-dependent (FIG. 3D). When hFc$_{\gamma 1}$ was substituted for the decoy receptors in proliferation assays, no abrogation of the fusion protein's stimulatory activity was observed, arguing against a functional role in this system for the Fc component of the decoy receptors. Taken together, these findings indicate that chimerization promotes optimal functionality in regards to GITR and OX40 triggering. In addition, no distinct functional difference between dimeric and trimeric anti-GITR Ab•OX40L was found, and for simplicity, all remaining studies show data where fusion protein purified from transfectants expressing trimeric anti-GITR Ab•OX40L or hFc$_{\gamma 1}$•OX40L were used.

Figure 4:
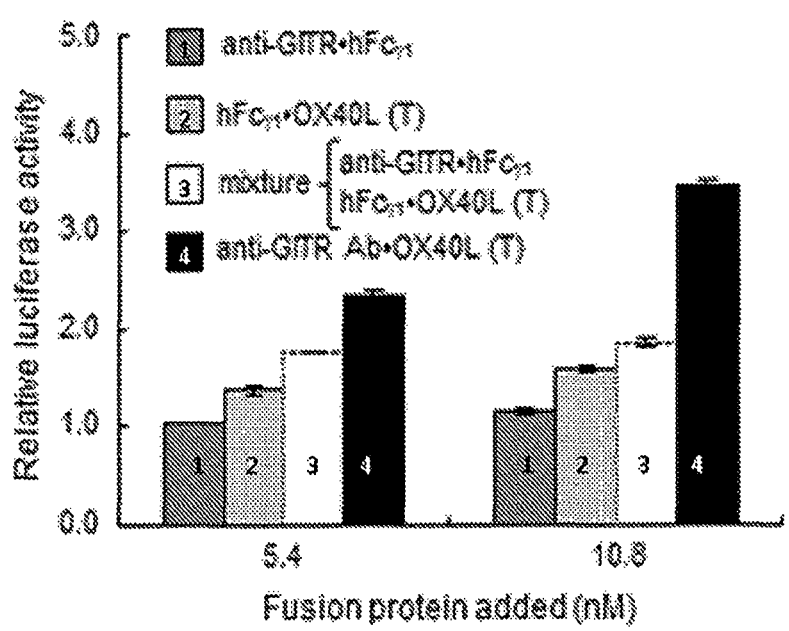
FIG. 4 depicts bar graphs indicating that anti-GITR Ab•OX40L fusion protein drives NF-κB-mediated transcription. HEK 293T cells co-transfected to express mouse GITR and OX40 receptors on their surface, were transfected with an NF-κB-luciferase reporter plasmid and transfection control construct [pNF-κB-Luc (5 µg) and phRL-TK (2 µg), respectively]. After 5 h, the cells were cultured in the presence of 1.25 and 2.5 µg/ml anti-GITR Ab•OX40L (5.4 and 10.8 nM, respectively) or fusion protein component ends at the same molar concentration. Cells were harvested and promoter activity of transfected plasmids measured using the Dual Luciferase Reporter assay system, normalizing firefly luciferase (pNF-κB-Luc) to the *Renilla* luciferase internal control (phRL-TK).

Several members of the TNF receptor family, including OX40 and GITR, activate the transcription factor NF-κB through cognate TNF receptor-associated (TRAF) proteins. Consequently, to mechanistically probe anti-GITR Ab•OX40L effects, experiments were designed to determine whether this fusion protein could up-regulate NF-κB-driven transcription. This was accomplished by co-transfecting a pNF-κB-luciferase reporter into HEK 293T cells stably transfected to co-express OX40 and GITR receptors. Relative luciferase activity, as a reflection of NF-κB activity, was measured in GITR-OX40/293T cotransfectants treated with 1.25 and 2.5 µg/ml (5.4 and 10.8 nM) anti-GITR Ab•OX40L. The fusion protein produced a dose-dependent increase in luciferase activity and was more active than its component parts, added alone or in combination (FIG. 4). To solidify the functional advantage provided by chimerization, it was separately demonstrated that when using GITR-only GITR/293T transfectants (lacking OX40), there was comparable enhancement of NF-κB activity by anti-GITR Ab•OX40L (T) and anti-GITR•hFc$_{\gamma 1}$. Significantly, since this experiment is being performed with stable transfectants that are adherent and non-lymphoid, it strengthens the notion that the anti-GITR Ab•OX40L fusion protein is functioning to bridge and co-signal through neighboring receptors on the same cell.

Anti-GITR Ab•OX40L Inhibits the Suppressive Activity of $CD4^+CD25^+$Treg Cells

Figure 5A:
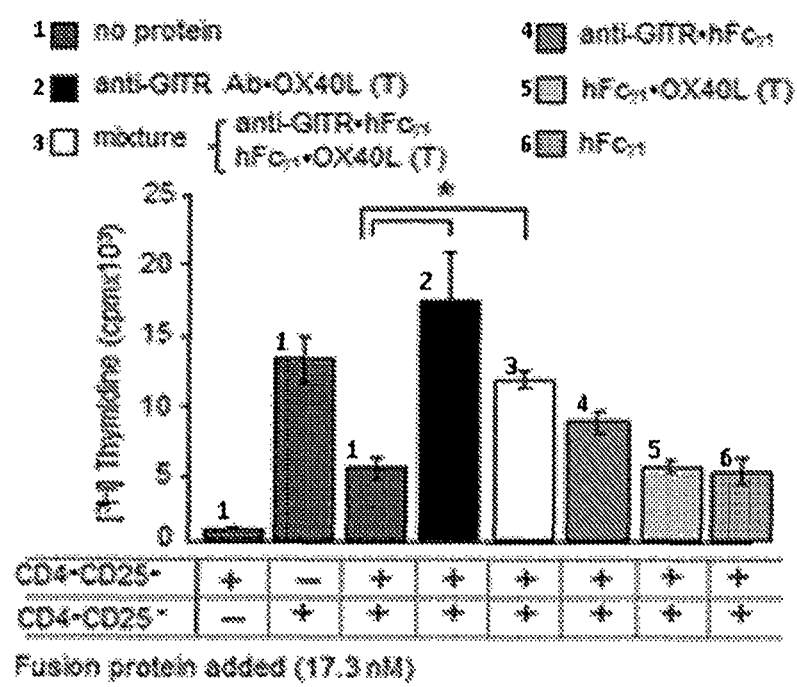
FIGS. 5A-5B, depicts bar graphs indicating that anti-GITR Ab•OX40L fusion protein inhibits Treg suppressive activity.

The presence of Treg cells within tumor microenvironments is believed to be a critical factor in blunting effective anti-tumor immune responses. Thus, turning now from Teff cells to highly purified Treg cells, the functional consequences of GITR and OX40 co-triggering induced by dual-signaling fusion protein were examined. Splenic $CD4^+$ $CD25^+$ Treg cells inhibited the proliferation of $CD4^+CD25^-$ T responder cells stimulated with soluble anti-CD3/28 and mytomycin C-treated APC by approximately 60%, and adding anti-GITR•hFc$_{\gamma 1}$ and hFc$_{\gamma 1}$•OX40L in combination partially reversed Treg suppression (FIG. 5A). However, adding a molar equivalent amount of anti-GITR Ab•OX40L (4 μg/ml) completely reversed the suppressive activity of CD4$^+$CD25$^+$ Treg cells and induce proliferation to levels higher than those observed with CD4$^+$CD25$^-$ T responder cells alone. Importantly, these studies show that combining GITR and OX40 triggering, either with anti-GITR Ab•OX40L or a mixture of individual triggers, negates suppression significantly more than anti-GITR•hFc$_{\gamma 1}$ alone, whereas hFc$_{\gamma 1}$•OX40L alone has no effect at these concentrations.

Figure 5B:
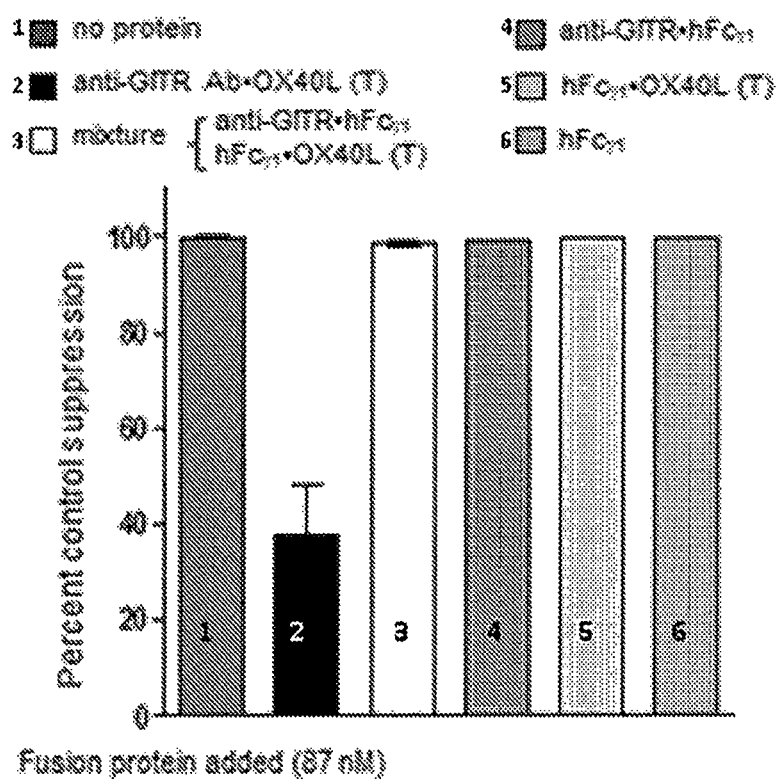

To dissect whether combined GITR and OX40 triggering is acting as a direct inhibitor of Treg suppressor function, and not merely stimulating Teff proliferation, fusion proteins were pre-incubated with CD4$^+$CD25$^+$ Treg cells, then washed, prior to culturing them with T responder cells (FIG. 5B). In this case, only anti-GITR Ab•OX40L neutralized Treg suppressive activity, suggesting that anti-GITR Ab•OX40L binds directly to Treg cells to block function. This result also suggests combined anti-GITR•hFc$_{\gamma 1}$ and hFc$_{\gamma 1}$•OX40L triggering of GITR and OX40 receptors on Treg surfaces is not effective at abrogating suppressive activity unless both receptors signal simultaneously, and point to a possible mechanism of fusion protein-mediated bridging of receptors on the same Treg cell.

Anti-GITR Ab•OX40L Suppresses CD25$^+$Foxp3$^+$ Treg Conversion

The source of immunosuppressive Treg within tumors is two-fold; arising from the recruitment and expansion of naturally occurring Treg and induced through the conversion of CD4$^+$Foxp3$^-$ T cell precursors in the presence of TGFβ. In this study, the simultaneous triggering of the OX40 and GITR axes was evaluated.

Figure 6A:
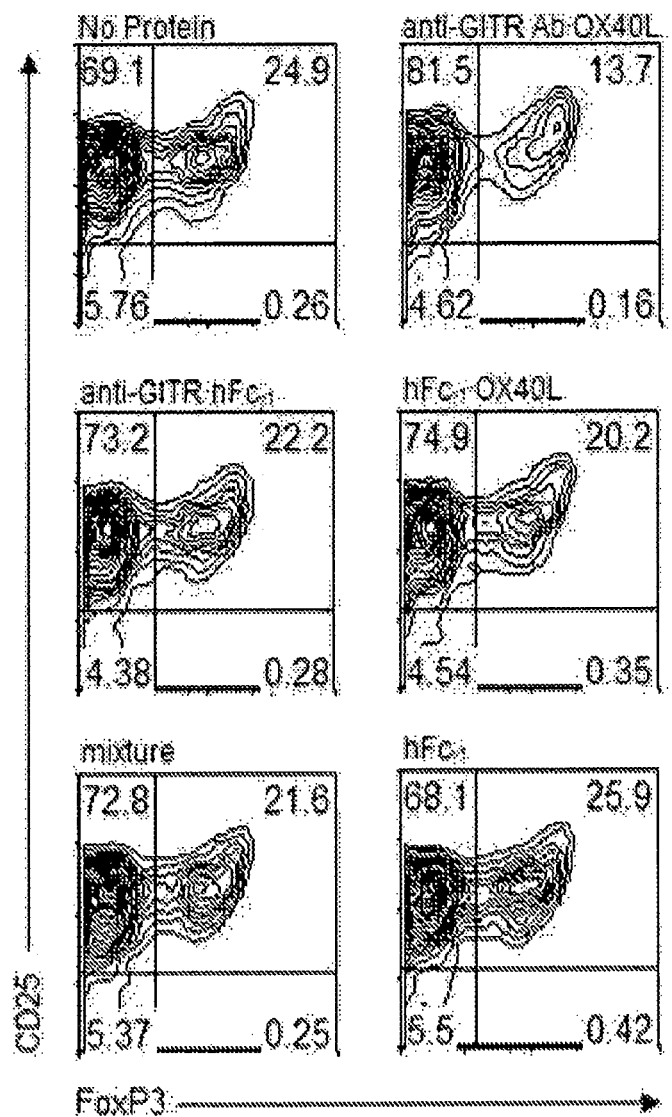
FIGS. 6A-6B, depicts histograms and a bar graph indicating that anti-GITR Ab•OX40L fusion protein inhibits $FoxP3^+$ Treg conversion.
Figure 6B:
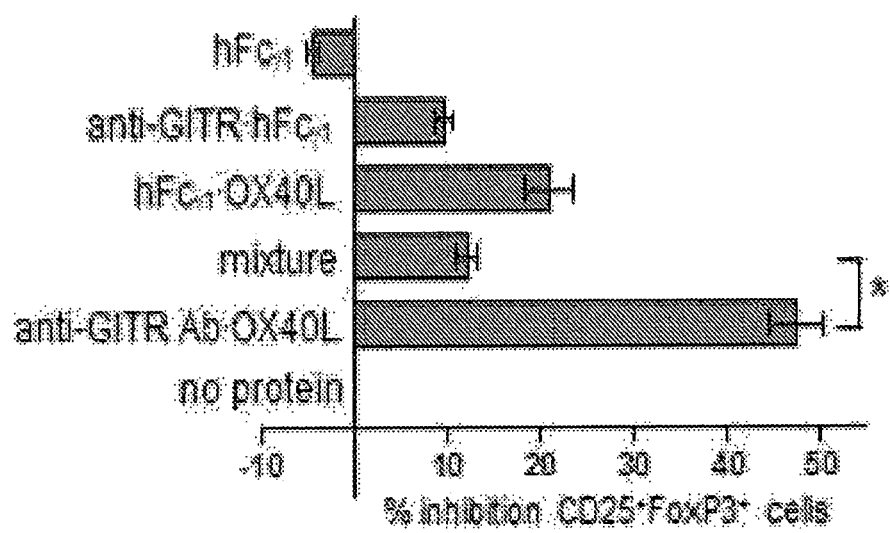

For this experiment, a system for in vitro generation of CD4$^+$CD25$^+$Foxp3$^+$ Treg cells from naïve precursors was used (Tone et al., 2008, Nat. Immunol. 9:194-202). In this system, between 20-40% of CD4$^+$CD25$^-$ T cells activated for 3 days in the presence of TGFβ convert to CD25$^+$Foxp3$^+$ Treg cells (FIG. 6A, no protein). The addition of anti-GITR Ab•OX40L at the start of the culture period inhibited Treg conversion up to 50%, whereas anti-GITR•hFc$_{\gamma 1}$ and hFc$_{\gamma 1}$•OX40L (or mAbs targeting GITR [DTA-1] or OX40 [OX-86] receptors), added separately or in combination, were much less effective at suppressing Treg generation (FIGS. 6A and 6B). As little as 1.0 μg/ml (4.3 nM) anti-GITR Ab•OX40L was able to inhibit Treg conversion and its activity was dose-dependent. Taken together, costimulation with combined GITR and OX40 signals may promote immune responses by (i) conferring resistance to Treg suppression (ii) inhibiting Treg suppressive activity, and (iii) inhibiting Treg induction.

Combined GITR and OX40 Triggering Enhances Anti-Tumor Immunity

Figure 7A:
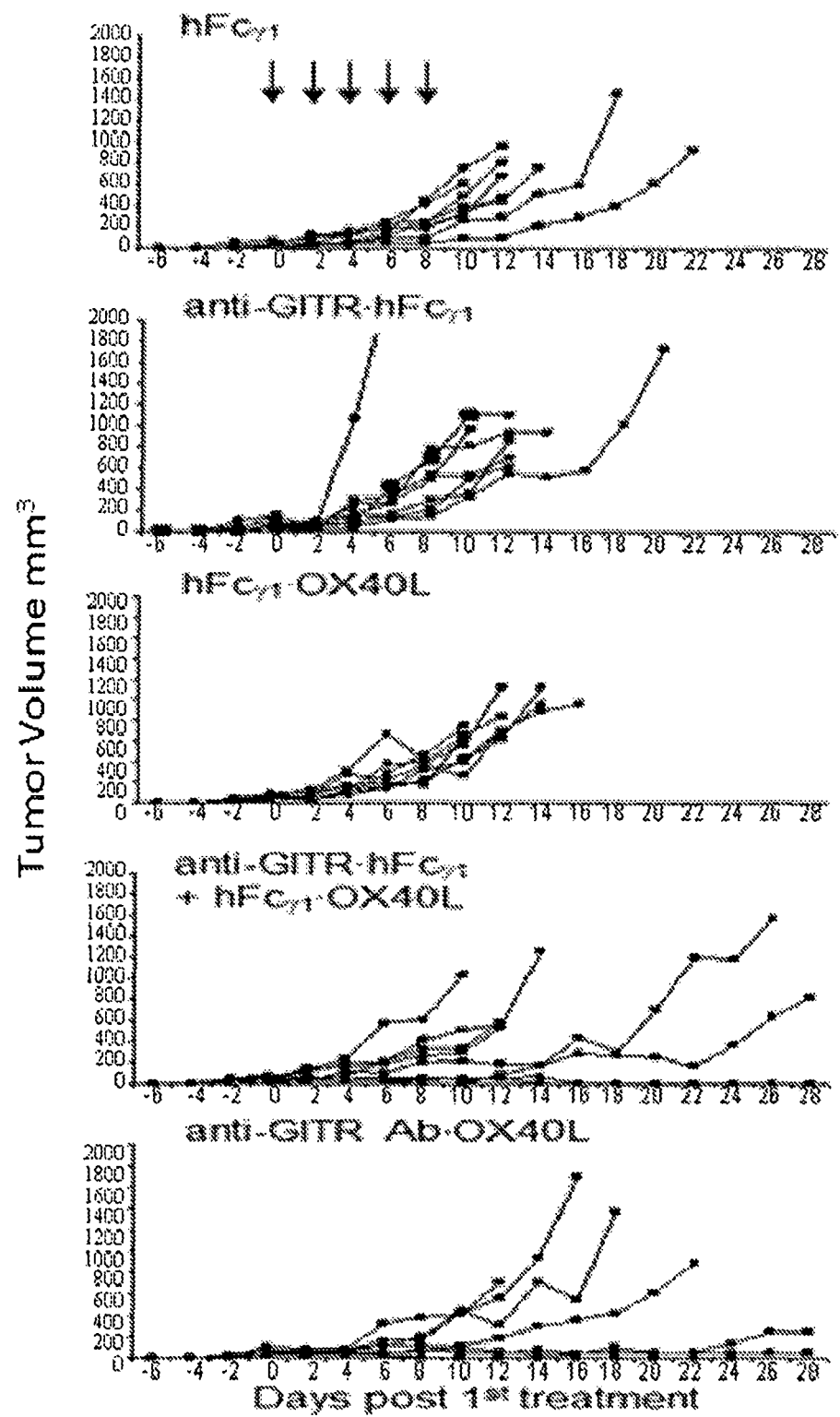
FIGS. 7A-7D, depicts graphs indicating that intratumoral anti-GITR Ab•OX40L treatment delays tumor progression and induces tumor rejection.
Figure 7B:
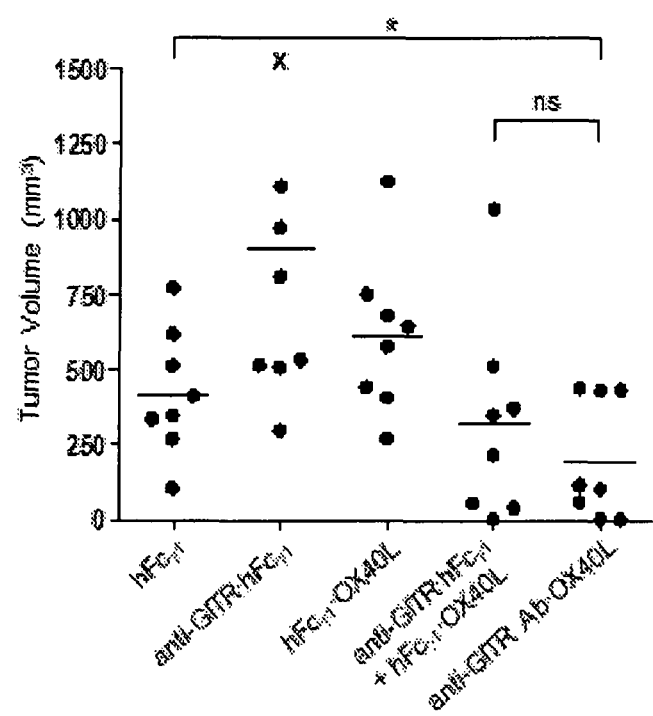
Figure 7C:
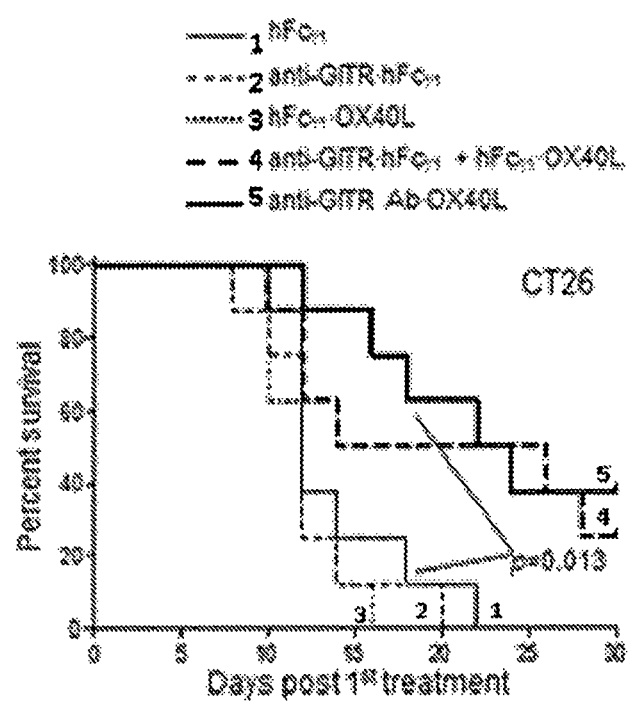

Having established in vitro that anti-GITR Ab•OX40L possesses greater activity than its component parts on both Teff and Treg cells, it was investigated whether this finding translates into enhancing immune responses in vivo. The vast majority of FoxP3$^+$ Treg cells infiltrating tumor beds express both OX40 and GITR (Piconese et al., 2008, J. Exp. Med. 205:825-839; Zhou et al., 2006, Blood 107:628-636). To this end, the CT26 colon carcinoma cell line was used to generate subcutaneous solid tumors in syngeneic BALB/c mice. Established tumors were treated, even though an immunization approach (i.e. treatment at the time of tumor injection) may have been more effective, in the interest of evaluating fusion protein-based anti-tumor therapeutic strategies. Intra-tumoral (i.t.) injections of anti-GITR Ab•OX40L or individual component parts, delivered separately or in combination, commenced when palpable tumors became evident (~10 mm$^3$), typically 6-10 days post CT26 seeding. Each group of mice received i.t. injections every other day for a total of 5 treatments. In the studies presented here, delivery of anti-GITR•hFc$_{\gamma 1}$ or hFc$_{\gamma 1}$•OX40L as single agents did not significantly inhibit tumor growth or promote survival compared to hFc$_{\gamma 1}$ (FIGS. 7A and 7B) or saline controls. On the other hand, combining anti-GITR•hFc$_{\gamma 1}$ and hFc$_{\gamma 1}$•OX40L (each at the same molar amount as single agents) slowed tumor growth and significantly enhanced survival, resulting in complete tumor rejection in 25% of mice (FIG. 7C). Even greater cure rates were achieved in preliminary studies where the concentration of each therapeutic, or the number of treatments delivered, was increased, and in those studies, agents delivered individually (e.g. hFc$_{\gamma 1}$•OX40L) also demonstrated anti-tumor effects, as previously shown by others. However for the studies shown here, the treatment amount was tailored to best demonstrate the disparity between mono- versus co-triggered GITR and OX40 receptors.

Figure 7D:
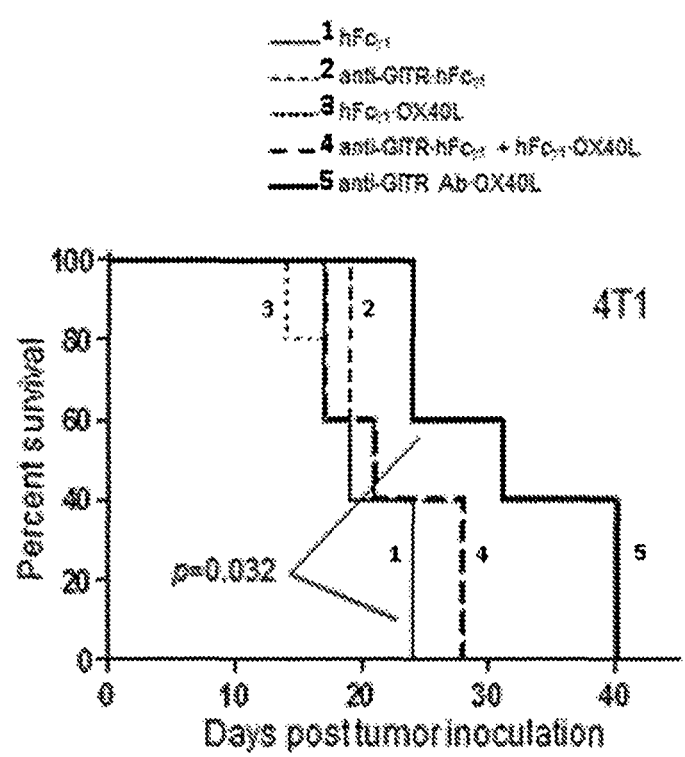

Chimeric anti-GITR Ab•OX40L was used to evaluate the effectiveness of simultaneously engaging GITR and OX40 receptors on the same cell. Intra-tumoral injection of anti-GITR Ab•OX40L (used at the same molar equivalent as single components) markedly slowed tumor growth and increased survival (FIGS. 7A, 7B, and 7C), however, anti-tumor responses were only marginally better than the combination of individual components. In a separate study, it was investigated whether the observed increase in anti-tumor responses mediated by combined GITR and OX40 triggering is more broadly applicable to other tumor types, specifically, an aggressive breast carcinoma cell line (4T1) injected subcutaneously to induce tumors in syngeneic BALB/c mice. Intra-tumoral injection of anti-GITR Ab•OX40L delayed tumor growth and significantly improved survival versus the hFc$_{\gamma 1}$ control (FIG. 7D). However, in contrast to the CT26 tumor model, treatment with anti-GITR•hFc$_{\gamma 1}$ and hFc$_{\gamma 1}$•OX40L, as individual or combined agents, was not significantly more effective than the control group (hFc$_{\gamma 1}$) and none of the treatment methods was completely effective at eliminating tumor in this model. Importantly, in contrast to studies using high doses of anti-GITR mAbs (Shimizu et al., 2002, Nat. Immunol. 3:135-142; Ko et al., 2005, J. Exp. Med. 202:885-891), i.t or i.v. treatment of mice with anti-GITR Ab•OX40L at all doses tested (up to 100 μg/close) did not elicit overt autoimmune disease. Together, these studies indicate that combinatorial treatments geared toward co-triggering GITR and OX40 receptors are more effective at inducing anti-tumor immune responses than mono-therapies and position chimeric dual-signaling fusion proteins as a possible new class of cancer immunotherapeutic agent.

Anti-GITR Ab•OX40L Enhances the Effector Function of CD8$^+$ CTL In Vivo

Figure 8:
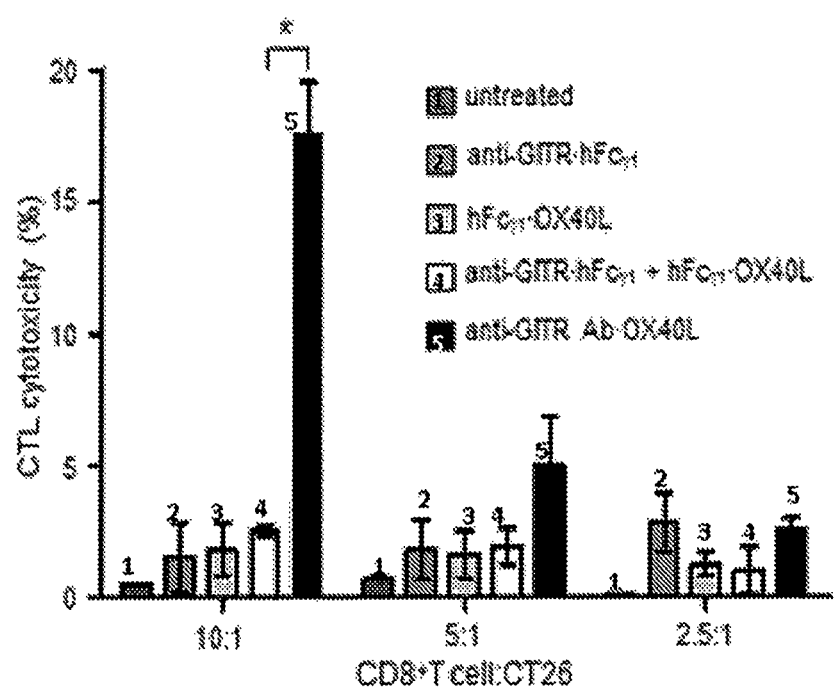
FIG. 8 depicts a bar graph indicating that anti-GITR Ab•OX40L induces CT26-specific $CD8^+T$ cell cytotoxicity in tumor bearing mice. BALB/c mice were inoculated with CT26 cells and treated with intratumoral injections of anti-GITR Ab•OX40L or control fusion proteins, as described in FIG. 7. On day 10 after the first treatment, $CD8^+T$ cells were isolated from the spleen and lymph nodes of tumor-bearing or naïve (untreated) mice and cultured in vitro for 4 h in 96-well round bottom plates with $5 \times 10^3$ CT26 cells at various $CD8^+T$ cell to CT26 cell effector:target ratios. LDH levels in culture supernatants were measured using a colorimetric cytotoxicity detection assay. Data are mean±SEM of 5 individual samples and are representative of two independent experiments. Significant difference (*, p<0.01) by two-sided Student's t test.

GITR and OX40 receptors are expressed by activated CD4$^+$ T helper (Th) cells and CD8$^+$ cytotoxic T lymphocytes (CTL) cells alike, and both cell types are essential for immune-mediated tumor regression (Yu and Fu, 2006, Lab. Invest. 86:231-245; Disis et al., 2009, Lancet 373: 673-683). In addition, anti-tumor cytolytic activity has been associated with tumor Ag-specific CD8$^+$ CTL killing (Kedar and Weiss, 1983, Adv. Cancer Res. 38:171-287; Whiteside, 2010, J. Allergy Clin. Immunol. 125:S272-83). To determine the effectiveness of simultaneous GITR and OX40 triggering on Th and CTL populations, proliferation was measured (as shown in FIG. 1), CTL killing and interferon (IFN)-γ secretion. CD8+ T cells were isolated from the spleens of tumor-bearing mice treated with i.t. injections of anti-GITR Ab•OX40L and individual components, delivered separately or in combination. Purified CD8+ T cells were mixed with CT26 tumor cell targets at various effector:target ratios (CD8+ T:CT26 of 10:1, 5:1, 2.5:1) and the release of lactate dehydrogenase (LDH) from lysed targets was used to evaluate the magnitude of tumor cell killing (Andre et al., 2004, J. Clin. Lab. Anal. 18:27-30). Splenic CD8+ CTL from anti-GITR Ab•OX40L treated mice, but not those treated with individual components (added alone or in combination), substantially increased tumor cell killing, especially at the highest effector:target ratio (FIG. 8). Lastly, T cells mediate tumor regression, in part, by producing Th1 cytokines such as IFN-γ (Ko et al., 2005, J. Exp. Med. 202:885-891; Fallarino and Gajewski, 1999, J. Immunol. 163:4109-4113). However, when it was tested whether anti-GITR Ab•OX40L or its component parts can costimulate IFN-γ production in isolated CD4+ and CD8+ T cells activated with immobilized anti-CD3, it was shown that anti-GITR Ab•OX40L is a potent inducer of IFN-γ secretion in both CD4+ and CD8+ T cells, but it did not demonstrate greater activity than individual ligand triggers, added alone or in combination. Taken together, these data suggest anti-GITR Ab•OX40L, by co-triggering GITR and OX40 receptors, acts primarily to increase the number and/or killing function of tumor antigen-specific Teff cells involved in tumor regression.

Multi-Functional Fusion Proteins

Multi-functional fusion proteins have emerged as useful agents for modulating both the generation and function of diverse immune cell types. Over the years, several new classes of fusion proteins for these purposes have been introduced, which feature abilities to convert intercellular signals, generate auto-signals at cell surfaces, and coordinately deliver dual signals to individual cells. The paradigmatic fusion proteins mediating these functions were designed primarily with single selected cell targets in mind By contrast, the chimeric protein of the present invention was designed for coordinate modulation of two distinct cellular subsets, and with an eye towards amplifying functional effects. For example, this protein co-triggers in a reinforcing way two receptors of the TNF receptor superfamily, GITR and OX40, and in so doing, inhibits Treg cells and activates Teff cells in parallel. This coordinate cellular modulatory capacity has yielded an intriguing new type of 'fusion protein immunoadjuvant', with downstream therapeutic potential in clinical contexts where immunopotentiation is desired, for example, vaccination and cancer treatment.

Anti-GITR Ab•OX40L was engineered by linking derivatives of an agonistic GITR-directed Ab and OX40L's extracellular domain, with the chimeric product capable of co-triggering GITR and OX40 receptors. While co-triggering can also be achieved by co-delivering the parental agonistic GITR-directed Ab and an $Fc_{\gamma 1}$ derivative of OX40L, the chimeric anti-GITR Ab•OX40L protein proved significantly more effective than the anti-GITR Ab+ $Fc_{\gamma 1}$•OX40L ligand mixture with respect to (1) inducing CD4+ T cell proliferation in vitro, (2) stimulating IL-2 production, (3) inducing NFκB transcriptional activity, (4) promoting CTL cytotoxic activity, (5) inhibiting the suppressive activity of CD4+ CD25+ Treg cells, and (6) inhibiting the generation CD4+ FoxP3+ Treg cells from Ag-induced naïve precursors. In addition, co-triggering of OX40 and GITR receptors, whether via anti-GITR Ab•OX40L or the Ab/ligand mixture, significantly enhanced anti-tumor efficacy against CT26 and 4T1 tumors.

Anti-GITR Ab•OX40L bridges OX40 and GITR receptors on the same cell and thereby yield functional synergy. The evidence for this synergy emerged from in vitro proliferation assays. $hFc_{\gamma 1}$•OX40L alone did little to enhance proliferation (FIGS. 2A and 3A). In contrast, anti-GITR•$hFc_{\gamma 1}$ alone did enhance CD4+ T cell proliferation, consistent with the established role of GITR triggering in TCR-induced T cell expansion (Nocentini et al., 2007, Eur. J. Immunol. 37:1165-1169). Thus, the predicted outcome of combined GITR and OX40 triggering would be their sum, that is, proliferation levels similar to GITR costimulation alone—and this was indeed the case for the mixture of $hFc_{\gamma 1}$•OX40L/anti-GITR•$hFc_{\gamma 1}$ (see FIG. 3A). However, linking the triggers within an anti-GITR Ab•OX40L fusion protein yielded nearly two-fold more proliferation than the mixture, consistent with the notion that bridging of adjacent receptors on T cells can augment efficacy. Furthermore, this chimerization advantage was reflected in other functional endpoints, such as IL-2 production (FIG. 3B) and NFκB signaling (FIG. 4).

Further evidence for enhanced fusion protein efficacy emerged from Treg-mediated suppression assays. At the concentrations used in this study, anti-GITR•$hFc_{\gamma 1}$ or $hFc_{\gamma 1}$•OX40L, used individually, did little to mitigate Treg suppressive activity. While adding them together did diminish Treg-mediated suppression (FIG. 5A), their fusion protein counterpart, anti-GITR Ab•OX40L, was significantly more effective, with the indication that it not only abrogates Treg suppression, but also simultaneously drives T responder cell proliferation. The notion that anti-GITR Ab•OX40L directly inhibits Treg activity was substantiated by the further observation that pre-treatment of Treg cells with this fusion protein, prior to co-culture with T responder cells, diminishes Treg suppressive potential (FIG. 5B). Notably, only the anti-GITR Ab•OX40L fusion protein, but not the combination of anti-GITR•$hFc_{\gamma 1}$ and $hFc_{\gamma 1}$•OX40L, was functional in this pre-treatment assay. This pre-treatment assay finding, along with the various other Treg data reported herein, serve to re-focus attention on the Treg cell as a primary target of OX40/GITR signaling. Some reports have argued that the lymphoid inhibition associated with signaling through GITR is simply a reflection of the desensitization of Teff cells to Treg modulation. The data disclosed herein suggest that an enhanced direct Treg effect can be elicited by co-triggering OX40 and GITR receptors, and only when the co-triggers are physically linked within a fusion protein.

The chimerization advantage was also apparent with respect to Treg generation. Triggering of OX40 individually, but not GITR, has been reported to suppress induced Treg conversion (Ndhlovu et al., 2004, Crit. Rev. Immunol. 24:251-266; So et al., 2008, Cytokine Growth Factor Rev. 19:253-262; Vu et al., 2007, Blood 110:2501-2510). At the concentrations used in this study, anti-GITR•$hFc_{\gamma 1}$ and $hFc_{\gamma 1}$•OX40L, added alone or in combination, showed minimal activity of this kind. By contrast, anti-GITR Ab•OX40L blocked Treg conversion up to 50%. Taken together, these findings demonstrate a chimerization advantage for this particular co-triggering pair across a variety of immune functional endpoints.

The results disclosed herein establish that co-triggering of the GITR and OX40L receptors is effective in the in vivo animal tumor model context, and is superior to single receptor triggering. Of special note in this regard is that treatment with anti-GITR Ab alone had no anti-tumor effect, and in fact led to tumors that were highly necrotic. Such necrotic tumors did not emerge when OX40 receptor triggering was added to the mix.

The findings shed some light on mechanisms, as reflected in the diverse set of observed co-triggering effects for this novel fusion protein. The constellation of enhanced in vitro functional activities associated with anti-GITR Ab•OX40L triggering raise the prospect that it may act in vivo to simultaneously activate various Teff subsets and inhibit the generation and function of Treg cells, thereby serving to tip the balance between immune effectors and regulators within tumor microenvironments. In vivo, simultaneous engagement of GITR and OX40 has the potential to: (i) expand the pool of the tumor Ag-specific Teff cells, (ii) enhance the cytotoxic activity of CD8+ CTLs and expand their numbers, (iii) inhibit Treg suppression, either directly, or by driving increased IL-2 production to counteract suppression (Shevach, 2009, Immunity 30: 636-645), and (iv) prevent the conversion of CD4+CD25− Th cells into Treg cells.

The present evaluation of anti-GITR Ab•OX40L points to the functional advantages of dual-signaling fusion proteins targeting lymphoid cells, whether effectors or regulators. Without wishing to be bound by any particular theory, it is believed that the fusion proteins of the invention can be used beyond lymphoid cells to other key immune effectors, such as antigen-presenting cells. For instance, there is the possibility of designing other dual-signaling proteins, with cis loop-back and/or bi-directional signaling capacities, that activate DC or inhibit the tolerogenic activity of tumor-associated macrophages. Thus, the future prospects for dual-signaling fusion proteins for cancer therapy are considerable.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A fusion protein comprising a first domain and a second domain, wherein the first domain comprises a portion of a binding moiety that binds to GITR, and wherein the second domain comprises a portion of a binding moiety that binds to OX40 receptor, wherein the fusion protein comprises an antibody fragment-ligand protein comprising the sequence of SEQ ID NO: 5.

2. A method of regulating immune cells, the method comprising contacting a populating of immune cells with the fusion protein of claim 1, wherein the population of immune cells comprises regulatory T (Treg) cells and effector T (Teff) cells, and further wherein the fusion protein:
   attenuates Treg suppressive function;
   inhibits Treg generation; or
   increases Teff cell proliferation, interleukin-2 production, and NF-κB signaling.

3. A method of modulating an immune response in a mammal in need thereof, the method comprising administering to the mammal a therapeutically effective amount of the fusion protein of claim 1, wherein said modulating an immune response comprises:
   attenuation of Treg suppressive function;
   inhibition of Treg generation; or
   an increase in Teff cell proliferation, interleukin-2 production, and NF-κB signaling.

4. A method of treating or ameliorating cancer in a mammal in need thereof, the method comprising administering to the mammal a therapeutically effective amount of the fusion protein of claim 1.

5. A method of enhancing an immune response to a cancer in a mammal in need thereof, the method comprising administering to the mammal a therapeutically effective amount of the fusion protein of claim 1.

6. A pharmaceutical composition comprising a pharmaceutically acceptable carrier and a fusion protein according to claim 1.

* * * * *